United States Patent [19]

DeBernardis et al.

[11] Patent Number: 5,049,564

[45] Date of Patent: Sep. 17, 1991

[54] 5-HT SELECTIVE AGENTS

[75] Inventors: John F. DeBernardis; Michael D. Meyer; Kevin B. Sippy, all of Lindenhurst, Ill.

[73] Assignee: Abbott Laboratories, Abbott Park, Ill.

[21] Appl. No.: 438,825

[22] Filed: Nov. 17, 1989

[51] Int. Cl.[5] .................. A61K 31/445; C07D 221/16
[52] U.S. Cl. ................................... 514/290; 514/232.8; 514/278; 544/126; 546/15; 546/16; 546/79; 546/93; 546/110; 546/111
[58] Field of Search ........................ 546/79, 15, 16, 93, 546/110, 111; 514/290, 278, 232.8; 544/126

[56] References Cited

U.S. PATENT DOCUMENTS

| 4,082,773 | 4/1978 | Hauck | 546/79 X |
| 4,578,393 | 3/1986 | Markwell | 514/310 |
| 4,824,852 | 4/1989 | Bottcher | 514/290 |

Primary Examiner—Mary C. Lee
Assistant Examiner—Jacqueline Haley
Attorney, Agent, or Firm—Jerry F. Janssen; Steven F. Weinstock

[57] ABSTRACT

Substituted 8-alkoxy-1,2,3,3a,8,8a-hexahydroindeno-[1,2-c]pyrroles; 5-alkoxy-2,3,4,4a,9,9a-hexahydro-1H-indeno[2,1-c]pyridines; and 9-alkoxy-2,3,3a,4,5,9a-hexahydro-1H-benz[e]isoindoles are selective 5-HT receptor agents and are thus useful in the treatment of anxiety, depression, and hypertension.

7 Claims, No Drawings

5-HT SELECTIVE AGENTS

BACKGROUND OF THE INVENTION

This invention relates to compounds and pharmaceutical compositions useful for the treatment anxiety, depression and hypertension. More particularly, this invention concerns certain novel 8-alkoxy-1,2,3,3a,8,8a-hexahydroindeno[1,2-c]pyrrole, 5-alkoxy-2,3,4,4a,9,9a-hexahydro-1H-indeno[2,1-c]pyridine, and 9-alkoxy-2,3,3a,4,5,9b-hexahydro-1H-benz[e]isoindole compounds useful in the treatment of anxiety, depression, and hypertension by virtue of their high affinity and selectivity for the 5-HT$_{1A}$ (5-hydroxytryptamine) subtype of serotonin receptors.

The serotonergic system exerts a complex and as yet not fully understood control over cardiovascular and CNS function. Multiple subtypes of the serotonin receptor have been described; and specific functions have been ascribed to certain of these subtypes which would indicate that pharmacological intervention would produce beneficial therapeutic results.

In particular, the 5-HT$_{1A}$ subtype of the serotonin receptor has been shown to exert significant control over the cardiovascular function, and may be involved as well in the etiology of anxiety and depression. Activation of centrally located 5-HT$_{1A}$ receptors has been shown to have an inhibitory effect on sympathetic outflow. Selective agonists of this receptor site have been shown to be efficacious in the treatment of hypertension in experimental animals. Although the precise mechanism of this antihypertensive effect has not been unequivocally determined, the currently available evidence suggests that this response to 5-HT$_{1A}$ selective agonists is mediated by decreased total peripheral resistance rather than decreased cardiac output. Therefore, modulation of central 5-HT$_{1A}$ receptors represents a novel and potentially useful method for the control of hypertension not found in any currently available drug.

The use of 5-HT$_{1A}$ selective agents in the treatment of anxiety has now become a clinically established principle. Again, the precise mechanisms by which these agents exert their anxiolytic effects have not been determined. Modulation of the serotonergic nervous system has become an equally well established principle for the treatment of depression, and current evidence has suggested that 5-HT$_{1A}$ selective agents may have therapeutic efficacy. Serotonergic abnormalities have been suggested for a variety of additional disease states such as, but not limited to, migraine, schizophrenia, dementia, eating disorders, sexual disorders, and nausea. Serotonic receptor subtype selective agents may find utility in the treatment of such disorders.

SUMMARY OF THE INVENTION

It has now been determined that the compounds of the present invention, as herein defined, demonstrate the ability to interact specifically with serotonin receptors and are thus useful as therapeutic agents in the treatment of hypertension, anxiety, and depression.

This invention relates to certain novel 8-alkoxy-1,2,3,3a,8,8a-hexahydroindeno[1,2-c]pyrrole, 5-alkoxy-2,3,4,4a,9,9a-hexahydro-1H-indeno[2,1-c]pyridine, and 9-alkoxy-2,3,3a,4,5,9b-hexahydro-1H-benz[e]isoindole compounds and to pharmaceutical compositions comprising these compounds. The present invention also provides a method for the treatment of anxiety, depression, hypertension and related disorders.

The compounds of this invention are represented by the formula

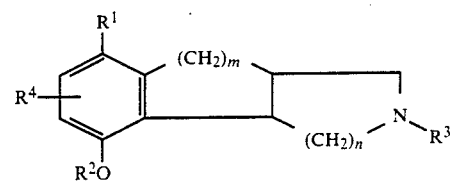

wherein
R$^1$ is hydrogen or an electron withdrawing group;
R$^2$ is hydrogen, lower alkyl, or aralkyl;
m and n are integers having a value of from 1 to 3;
R$^4$ is a member selected from the group consisting of hydrogen, halogen, lower alkyl, lower alkoxy, and aralkyl;
R$^2$ and R$^4$ taken together form an alkylenedioxy bridge;
R$^3$ is a member selected from the group consisting of hydrogen, lower alkyl, lower alkoxy, aralkyl, arylamidoalkylidene, arylalkylene, aryl(lower alkyl)amidoalkylidene, aryl(lower alkyl)amidoalkylene, benzoalkylenedioxyalkylene,
a) a group of the formula:

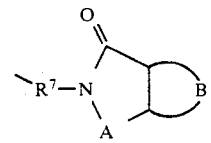

wherein
B is benzo, cyclohexyl, or a bicyclo ring;
A is CO, SO, or SO$_2$, and
R$^7$ is a bivalent aliphatic hydrocarbon;
b) a group of the formula:

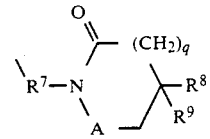

wherein q is an integer of from 0 to 3, R$^8$ and R$^9$ are hydrogen or lower alkyl, or R$^8$ and R$^9$ taken together form a ring of from 5 to 7 members and A and R$^7$ are as defined above; and
c) a group of the formula:

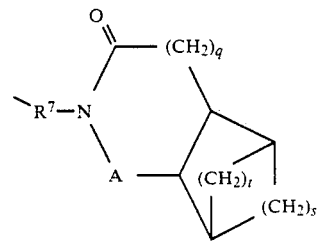

wherein
s and t are independent integers of from 1 to 3, and q, A, and R$^7$ are as defined above;

with the proviso that when $R^3$ is hydrogen, lower alkyl, or benzo(alkylenedioxy)alkylene and n is 1, m is other than 2;

and the pharmaceutically acceptable salts thereof.

DETAILED DESCRIPTION OF THE INVENTION

The present invention provides novel compounds which demonstrate a high affinity and selectivity for 5-HT$_{1A}$ subtype of serotonin receptors. This selectivity allows for the usefulness of the compounds for treating hypertension, anxiety, and depression.

The serotonergic nervous system plays a significant role in the control of various disease states including, but not limited to, hypertension, anxiety, and depression. Selective central activation of the 5-HT$_{1A}$ receptor sub-population results in decreased sympathetic outflow, which can cause lowering of blood pressure, total peripheral resistance, and heart rate. Blockade, or partial blockade of this receptor sub-population results in alteration of serotonergic neuronal activity which is beneficial in the treatment of anxiety and depression.

The compounds of this invention are represented by the formula:

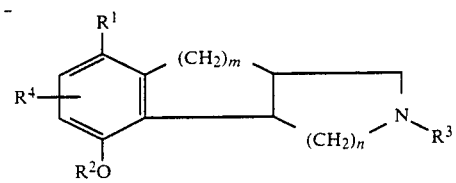

I wherein
$R^1$ is hydrogen or an electron withdrawing group;
$R^2$ is hydrogen, lower alkyl, or aralkyl;
m and an are integers having a value of from 1 to
$R^4$ is a member selected from the group consisting of hydrogen, halogen, lower alkyl, lower alkoxy, and aralkyl;
$R^2$ and $R^4$ taken together form an alkylenedioxy bridge;
$R^3$ is a member selected from the group consisting of hydrogen, lower alkyl, lower alkoxy, aralkyl, arylamidoalkylidene, arylalkylene, aryl(lower alkyl)amidoalkylidene, aryl(lower alkyl)amidoalkylene, benzoalkylenedioxyalkylene, a) a group of the formula:

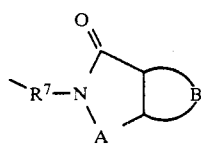

wherein
B is benzo, cyclohexyl, or a bicyclo ring;
A is CO, SO, or SO$_2$, and
b) a group of the formula:

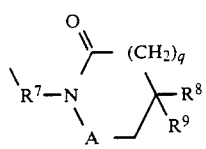

wherein q is an integer of from 0 to 3, $R^8$ and $R^9$ are hydrogen or lower alkyl, or $R^8$ and $R^9$ taken together form a ring of from 5 to 7 members and A and $R^7$ are as defined above; and c) a group of the formula:

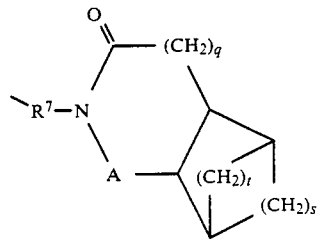

wherein
s and t are independent integers of from 1 to 3, and l, A, and $R^7$ are as defined above;

with the proviso that when $R^3$ is hydrogen, lower alkyl, or benzo(alkylenedioxy)alkylene and n is 1, m is other than 2;

and the pharmaceutically aceptable salts thereof.

This invention is also directed to pharmaceutical compositions and methods of treating anxiety, depression, hypertension, and related disorders.

Preferred compounds of the present invention are those wherein m is 1 and n is 1, prepresented by the formula:

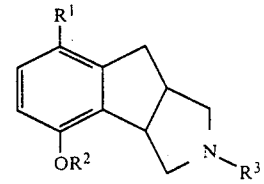

compounds wherein m is 2 and n is 1; represented by the formula:

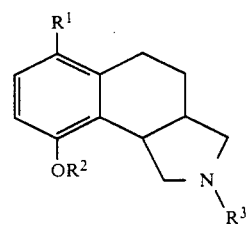

and compounds wherein m is 1 and n is 2, which are represented by the formula:

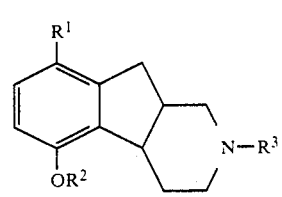

where $R^3$ is selected from:

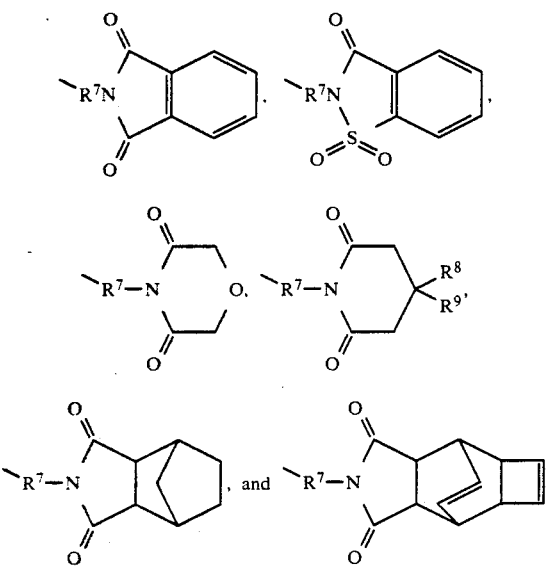

Various substituents including the benzo, clyclohexyl and bicyclic rings, the hexahydropyridine-1,3-dione ring system, and the cyclized $R^8$-$R^9$ rings may all be optionally substituted.

Compounds contemplated as falling within the scope of the present invention include, but are not limited to the following examples:

8-Hydroxy-2-methyl-1,2,3,3a,8,8a-hexahydroindeno[1,2-c]pyrrole;
8-Methoxy-2-methyl-1,2,3,3a,8,8a-hexahydroindeno[1,2-c]pyrrole;
8-Hydroxy-2-ethyl-1,2,3,3a,8,8a-hexahydroindeno[1,2-c]pyrrole;
8-Methoxy-2-ethyl-1,2,3,3a,8,8a-hexahydroindeno[1,2-c]pyrrole;
8-Hydroxy-2-propyl-1,2,3,3a,8,8a-hexahydroindeno-1,2-c]pyrrole;
S-Methoxy-2-aminomethyl-1,2,3,3a,8,8a-hexahydroindeno-[1,2-c]pyrrole;
8-Methoxy-2-cyanomethyl-1,2,3,3a,8,8a-hexahydroindeno-[1,2-c]pyrrole;
2-(R-1,4-Benzodioxanyl-2-methyl)-8-methoxy-1,2,3,3a,8,8a-hexahydroindeno[1,2-c]pyrrole;
2-(S-1,4-Benzodioxanyl-2-methyl)-8-methoxy-1,2,3,3a,8,8a-hexahydroindeno[1,2-c]pyrrole;
8-Methoxy-2-((2-phenyl)ethyl)-1,2,3,3a,8,8a-hexahydroindeno[1,2-c]pyrrole;
2-(3-(3,3-Tetramethylene)glutarimidyl)propyl)-8-hydroxy-1,2,3,3a,8,8a-hexahydroindeno[1,2-c]pyrrole;
2-(3-(3,3-Tetramethylene)glutarimidyl)propyl)-8-methoxy-1,2,3,3a,8,8a-hexahydroindeno-[1,2-c]pyrrole;
2-(4-(3,3-Tetramethylene)glutarimidyl)butyl-8-hydroxy-1,2,3,3a,8,8a-hexahydroindeno-[1.2-c]pyrrole;
2-(4-(3,3-Dimethyl)glutarimidyl)butyl-8-methoxy-1,2,3,3a,8,8a-hexahydroindeno[1.2-c]pyrrole;
2-(4-(3,3-Tetramethylene)glutarimidyl)butyl-8-methoxy-1,2,3,3a,8,8a-hexahydroindeno-[1,2-c]pyrrole;
2-(4-(3,3-Tetramethylene)glutarimidyl)butyl-5-chloro-8-hydroxy-1,2,3,3a,8,8a-hexahydro-indeno[1.2-c]pyrrole;
2-(4-(3,3-Tetramethylene)glutarimidyl)butyl-5-chloro-8-methoxy-1,2,3,3a,8,8a-hexahydro-indeno[1.2-c]pyrrole;
2-(5-(3,3-Tetramethylene)glutarimidyl)pentyl-8-methoxy-1,2,3,3a,8,8a-hexahydroindeno[1,2-c]pyrrole;
2-(4-(3,3-Tetramethylene)glutarimidyl)cis-buten-2-yl-8-methoxy-1,2,3,3a,8,8a-hexahydro[1,2-c]pyrrole;
2-(4-(3,3-Tetramethylene)glutarimidyl)trans-buten-2-yl-8-methoxy-1,2,3,3a,8,8a-hexahydro[1,2-c]pyrrole;
8-Hydroxy-2-(2-(4-Fluorobenzamido)ethyl)-1,2,3,3a,8,8a-hexahydroindeno[1,2-c]pyrrole;
8-Methoxy-2-(2-(4-Fluorobenzamido)ethyl)-1,2,3,3a,8,8a-hexahydroindeno[1,2-c]pyrrole;
8-Hydroxy-2-(4-(2-(1,2-Benzoisothiazolin-3-one-1,1-dioxide))butyl-1,2,3,3a,8,8a-hexahydroindeno[1,2-c]pyrrole;
8-Methoxy-2-(4-(2-(1,2-Benzoisothiazolin-3-one-1,1-dioxide))butyl-1,2,3,3a,8,8a-hexahydroindeno[1,2-c]pyrrole;
8-Hydroxy-2-(2-(2-phthalimido)butyl)-1,2,3,3a,8,8a-hyxahydroindeno-[1,2-c]pyrrole;
8-Methoxy-2-(2-(2-phthalimido)butyl)-1,2,3,3a,8,8a-hexahydroindeno-[1,2-c]pyrrole;
cis-9-Methoxy-2,3,4,4a,9,9a-hexahydro-1H-benz[e]isoindole;
trans-9-Methoxy-2,3,4,4a,9,9a-hexahydro-1H-benz[e]isoindole;
cis-9-Methoxy-2-propyl-2,3,4,4a,9,9a-hexahydro-1H-benz[e]isoindole;
trans-9-Methoxy-2-propyl-2,3,4,4a,9,9a-hexahydro-1H-benz[e]isoindole;
cis-9-Hydroxy-2-propyl-2,3,4,4a,9,9a-hexahydro-1H-benz[e]isoindole;
trans-9-Hydroxy-2-propyl-2,3,4,4a,9,9a-hexahydro-1H-benz[e]isoindole;
cis-2-(4-(3,3-Tetramethylene)glutarimidyl)butyl-9-hydroxy-2,3,3a,4,5,9b-hexahydro-1H-benz[e]isoindole;
cis-2-(4-(3,3-Tetramethylene)glutarimidyl)butyl-9-methoxy-2,3,3a,4,5,9b-hexahydro-1H-benz[e]isoindole;
trans-2-(4-(2-(1,2-benzisothiazolin-3-one-1,1-dioxide))-butyl)-9-methoxy-2,3,3a,4,5,9b-hexahydro-1H-benz[e]isoindole;
trans-2-(4-(3aα,4a,5,6,7a,7α-hexahydro-4,7-methano-1H-isoindol-1,3(2H)-dionyl)-butyl-9-methoxy-2,3,3a,4,5,9b-hexahydro-1H-benz[e]isoindole;
trans-2-(4-(3,3-tetramethylene)glutarimidyl)propyl-9-methoxy-2,3,3a,4,5,9b-hexahydro-1H-benz[e]isoindole;
trans-2-(4-(3a,4,4a,6a,7,7a-hexahydro-4,7-etheno-1H-cyclobut[f]isoindol-1,3-dionyl)-butyl-9-methoxy-2,3,3a,4,5,9b-hexahydro-1H-benz[e]isoindole;
trans-2-((S)-α-methylbenzyl)-9-methoxy-2,3,3a,4,5,9b-hexahydro-1H-benz[e]isoindole;
trans-2-(2-aminoethyl)-9-methoxy-2,3,3a,4,5,9b-hexahydro-1H-benz[e]isoindole;
trans-2-(3-aminopropyl)-9-methoxy-2,3,3a,4,5,9b-hexahydro-1H-benz[e]isoindole;
(−)-trans 9-methoxy-2,3,3a,4,5,9b-hexahydro-1H-benz[e]isoindole;
(+)-trans 9-methoxy- 2,3,3a,4,5,9b-hexahydro-1H-benz[e]isoindole;
trans 9-methoxy-2-(2-(4-fluorobenzamido)ethyl)-2,3,3a,4,5,9b-hexahydro-1H-benz[e]isoindole;
trans 9-methoxy-2-(3-(4-fluorobenzamido)propyl)-2,3,3a,4,5,9b-hexahydro-1H-benz[e]isoindole;

trans-2-(3-(2-(1,2-benzisothiazolin-3-one-1,1-dioxide))-propyl)-9-methoxy-2,3,3a,4,5,9b-hexahydro-1H-benz[e]isoindole;

cis-2-(4-(2-(1,2-benzisothiazolin-3-one-1,1-dioxide))-butyl)-9-methoxy-2,3,3a,4,5,9b-hexahydro-1H-benz[e]isoindole;

cis-2-(3-(3,3-tetramethylene)glutarimidyl)-propyl-9-methoxy-2,3,3a,4,5,9b-hexahydro-1H-benz[e]isoindole;

cis-2-(3-(2-(1,2-benzisothiazolin-3-one-1,1-dioxide))-propyl)-9-methoxy-2,3,3a,4,5,9b-hexahydro-1H-benz[e]-isoindole;

trans-2-(4-(3a,4,4a,5,6,6a,7,7a-octahydro-4,7-ethano-1H-cyclobut[f]isoindol-1,3-dionyl)butyl)-9-methoxy-2,3,3a,4,5,9b-hexahydro-1H-benz[e]isoindole;

(−)-trans-2-(4-(3a,4,4a,6a,7,7a-hexahydro-4,7-etheno-1H-cyclobut[f]isoindol-1,3-dionyl)butyl)-9-methoxy-2,3,3a,4,5,9b-hexahydro-1H-benz[e]isoindole;

(+)-trans-2-(4-(3a,4,4a,6a,7,7a-hexahydro-4,7-etheno-1H-cyclobut[f]isoindol-1,3-dionyl)butyl)-9-methoxy-2,3,3a,4,5,9b-hexahydro-1H-benz[e]isoindole;

cis-2-Benzyl-5-methoxy-2,3,4,4a,9,9a-hexahydro-1H-indeno[2,1-c]pyridine;

trans-2-Benzyl-5-methoxy-2,3,4,4a,9,9a-hexahydro-1H-indeno[2,1-c]pyridine;

cis-5-Methoxy-2,3,4,4a,9,9a-hexahydro-1H-indeno[2,1-c]pyridine;

trans-5-Methoxy-2,3,4,4a,9,9a-hexahydro-1H-indeno[2,1-c]pyridine;

cis-5-Methoxy-2-propyl-2,3,4,4a,9,9a-hexahydro-1H-indeno[2,1-c]pyridine;

cis-5-Hydroxy-2-propyl-2,3,4,4a,9,9a-hexahydro-1H-indeno[2,1-c]pyridine;

trans-5-Methoxy-2-propyl-2,3,4,4a,9,9a-hexahydro-1H-indeno[2,1-c]pyridine;

cis-2-(3,3-Tetramethylene)glutarimidyl)propyl-5-methoxy-2,3,4,4a,9,9a-hexahydro-1H-indeno[2,1-c]pyridine;

trans-2-(3,3-Tetramethylene)glutarimidyl)propyl-5-methoxy-2,3,4,4a,9,9a-hexahydro-1H-indeno[2,1-c]pyridine;

cis-2-(3,3-Tetramethylene)glutarimidyl)butyl-5-methoxy-2,3,4,4a,9,9a-hexahydro-1H-indeno[2,1-c]pyridine;

trans-2-(3,3-Tetramethylene)glutarimidyl)butyl-5-methoxy-2,3,4,4a,9,9a-hexahydro-1H-indeno[2,1-c]pyridine;

trans-2(3-(2-(1,2-benzisothiazolin-3-one-1,1-dioxide))-propyl)-5-methoxy-2,3,4,4a,9,9a-hexahydro-1H-indeno[2,1-c]pyridine;

trans-2(4-(2-(1,2-benzisothiazolin-3-one-1,1-dioxide))-butyl)-5-methoxy-2,3,4,4a,9,9a-hexahydro-1H-indeno[2,1-c]pyridine;

trans-2-(2-(4-fluorobenzamido)ethyl)-5-methoxy-2,3,4,4a,9,9a-hexahydro-1H-indeno[2,1-c]pyridine hydrochloride;

As used throughout this specification and the appended claims, the term "optionally substituted" shall mean a group or radical that is substituted with halogen, lower alkyl, mono- or di(lower alkyl)-substituted lower alkyl, (lower alkyl)thio, halo-substituted lower alkyl, amino-substituted lower alkyl, mono- or di(lower alkyl)-substituted amino, lower alkenyl, lower alkynyl, halogen, lower alkoxy, aryloxy, aryl(lower alkyl), hydroxy, cyano, amino, mono- and di(lower alkyl)amino, or nitro.

The term "lower alkyl" refers to branched or unbranched saturated hydrocarbon radicals having from one to six carbon atoms. Representatives of such groups are methyl, ethyl, propyl, iso-propyl, butyl, sec-butyl, iso-butyl, tert-butyl, pentyl, neo-pentyl, iso-pentyl, tert-pentyl, iso-hexyl, and the like.

The term "alkenyl" denotes a branched or unbranched monovalent hydrocarbon radical containing at least one carbon-carbon double bond, such as ethenyl (—CH=CH$_2$), propenyl (—CH$_2$—CH=CH$_2$), and the like.

The term "alkylidene" refers to a divalent branched or unbranched hydrocarbon radical containing at least one carbon-carbon double bond. Examples include ethylidene (—CH=CH—), propylidene (—CH$_2$CH=CH—), and the like.

The term "alkynyl" refers to a monovalent branched or unbranched hydrocarbon radical containing at least one carbon-carbon triple bond, for example ethynyl, propynyl, and the like.

The term "lower alkoxy" denotes an alkyl group as defined above, attached to the parent molecular moiety through an oxygen atom. Representatives of such groups include methoxy, ethoxy, butyoxy, and the like.

The term "(lower alkyl)thio" refers to a lower alkyl group as defined above, attached to the parent molecular moiety through a sulfur atom. Typical (lower alkyl)thio groups include methylthio, ethylthio, propylthio, iso-propylthio, and the like.

The terms "halo-" and "halogen" refer to a substituent selected from fluoro-, chloro-, bromo-, and iodo-.

The term "aryl" as used herein refers to mono- or polycyclichydrocarbon fused or nonfused aromatic ring systems which may contain one or more hetero atoms such as oxygen, nitrogen, or sulfur in the ring system and which may be optionally substituted as defined hereinabove. Representative aryl groups are phenyl, naphthyl, biphenylene, triphenyl, pyridyl, pyrrolyl, furyl, thienyl, indolyl, pyrazyl, iso-quinolyl, thiazolyl, imidazolyl, oxazolyl, puryl, phenazyl, carbazolyl, and the like. The term "arylalkyl" as used herein refers to a substituted or unsubstituted aryl ring system as defined above attached to a lower alkyl radical as defined above. Such groups include, but are not limited to benzyl, quinolyl, thiazolyl, imidazolyl, oxazolyl, puryl, phenazyl, carbazolyl, and the like.

The term "alkylenedioxy" as used herein refers to a divalent radical of the form —O—X—O— wherein X is methylene (—CH$_2$—), ethylene (—CH$_2$CH$_2$—), trimethylene (—CH$_2$CH$_2$CH$_2$—), carbonyl (>C=O), or sulfonyl (>S=O).

The term "benzoalkylenedioxoalkylene" as used herein refers to the structure

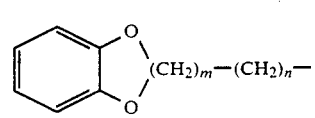

where m and n are independently 1 or 2.

The terms "arylamidoalkylidene" and "arylamidoalkylene" refer, respectively, to the structures aryl—CO—NH—(alkylidene)— and aryl—CO—NH—(alkylene)— wherein aryl, alkylidene, and alkylene are as defined above.

The terms "aryl(lower alkyl)amidoalkylidene" and "aryl(lower alkyl)amidoalkylene" refer, respectively, to groups having the structures aryl(lower alkyl)—CO—NH—alkylidene and aryl(lower alkyl- )—CO—NH—alkylene, with aryl, alkylene, and alkylidene as defined above.

The terms "bicyclo" and "bicyclic ring" refer to groups of the formula

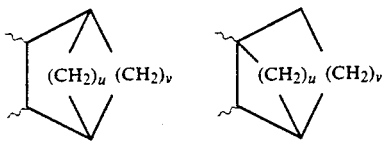

where u and v are independent integers having a value of from 1 to 3.

The terms "bivalent aliphatic hydrocarbon" and "divalent aliphatic hydrocarbon" refer to radicals derived from saturated and unsaturated, branched and unbranched acyclic hydrocarbons of from one to twelve carbon atoms and having two free valence bonds. Such groups include methylene, ethylene, propylene, methylethylene, ethylethylene, 4-methyl-2-pentylene, and the like.

The term "electron withdrawing groups" as used herein means substituent groups which have an inductive electron withdrawing effect greater than that of hydrogen. Hammet substituent sigma constants for various substituent groups, calculated for the ionization of meta-substituted benzoic acids provide a useful means of predicting relative electron withdrawing inductive effects, and are well known to those familiar with physical organic chemistry. See, for example, Hine, *Physical Organic Chemistry*, McGraw-Hill Book Co., New York, 1962, pp. 85-88.

Those substituent groups having a greater electron-withdrawing inductive effect than hydrogen have positive Hammett sigma constants. Those substituents which exhibit a lesser inductive electron-withdrawing effect than hydrogen possess negative sigma constants.

Representative electron-withdrawing substituents are halo, mercapto, acylmercapto such as acetylmercapto, alkylsulfido such as methylsulfido ($CH_3S—$), nitro, cyano, keto groups such as acetyl, halomethyl such as chloromethyl, and alkoxyalkylene groups such as methoxymethylene ($CH_3OCH_2—$).

The term "pharmaceutically aceptable salts" refers to the relatively non-toxic, inorganic and organic acid addition salts and, where the compounds of this invention also contain an acidic functional group, the alkali and alkaline earth metal salts. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, laurylsulphonate salts and the like.

Representative alkali or alkaline earth salts include the sodium, potassium, calcium, and magnesium salts and the like.

Certain of the compounds of this invention may exist in cis-/trans-isomeric forms and/or possess one or more chiral centers and may exist in optically active forms. This invention contemplates all isomeric forms of the compounds including cis-/trans-isomers as well as individual optical isomers and mixtures thereof.

The present invention also provides pharmaceutical compositions which comprise one or more of the compounds of formula I above formulated together with one or more non-toxic pharmaceutically acceptable carriers. The pharmaceutical compositions may be specially formulated for oral administration in solid or liquid form, for parenteral injection, or for rectal administration.

The pharmaceutical compositions of this invention can be administered to humans and other animals orally, rectally, parenterally (i.e. intravenously, intramuscularly, or sub-cutaneously), intracisternally, intravaginally, intraperitoneally, topically (as by powders, ointments, or drops), bucally, or as an oral or nasal spray.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous cariers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like, Prolonged absorption of the injectable pharmaceutical form may be brought about by the inclusion of agents which delay abdorption such as aluminum monostearate and gelatin.

If desired, and for more effective distribution, the compounds can be incorporated into slow release or targeted delivery systems such as polymer matrices, liposomes, and microspheres.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alignates, gelatin, polyvinylpyrrolidone, surcrose, and acacia, c) humectants such as glycerol, d) disintegrating agents such as agar-agar, calcium carbonate, potato ortapioca starch, alginic acid, certain silicates, and sodium carbonate, e) solution retarding agents such as paraffin, f) absorption accelerators such as quaternaryammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in microencapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Dosage forms for topical administration of a compound of this invention include powders, sprays, ointments and inhalants. The active compound is mixed under sterile conditions with a pharmaceutically acceptable carrier and any needed preservatives, buffers, or propellants which may be required. Opthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved. Generally dosage levels of about 0.1 to about 200, more preferably of about 0.5 to about 150, and most preferably about 1 to about 125 mg of active compound per kilogram of body weight per day are administered orally to a mammalian patient suffering from hypertension. If desired, the effective daily dose may be divided into multiple doses for purposes of administration, e.g. two to four separate doses per day.

The compounds of this invention are prepared by the methods generally depicted in Reaction Schemes I, II, III, and IIIa below.

Referring to Reaction Scheme I, the ester 1 is treated with potassium t-butoxide in ether, followed by condensation with diethyl oxalate to yield the keto-diester 2. Cyclization of 2 in PPA at room temperature affords the unsaturated diester 3, which upon catalytic hydrogenation yields the diester 4. The diester is converted to the N-benzyl diamide by treatment with excess of a 1:1 complex of trimethyl aluminum and benzyl amine, which upon treatment with one equivalent of para-toluenesulfonic acid in refluxing xylene yields the imide 5. Borane reduction to the tertiary amine (6) followed by hydrogenolysis yields the key intermediate 7. This intermediate is treated with variously substituted alkyl bromides in acetonitrile in the presence of ethyl diisopropyl amine to yield the final products (8) described in this patent application.

Scheme I
Synthesis of 8-Alkoxy-1,2,3,3a,8,8a-hexahydroindeno[1,2-c]pyrroles

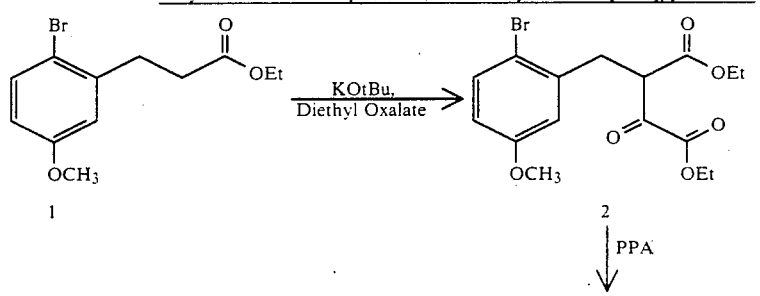

Scheme I
Synthesis of 8-Alkoxy-1,2,3,3a,8,8a-hexahydroindeno[1,2-c]pyrroles

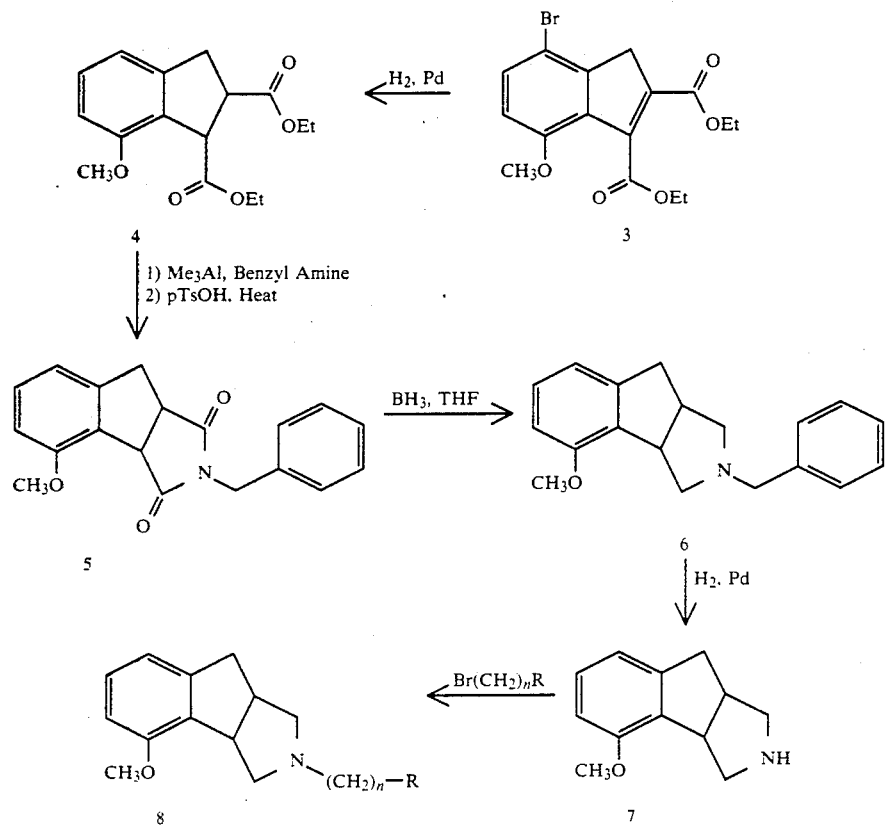

Referring to Reaction Scheme II, cyclization of the acid 1 in polyphosphoric acid at 90° C. yields the indanone 2. Treatment of the indanone with triethyl orthoformate in the presence of boron trifluoride etherate, followed by ethyl diisopropyl amine yields the acetal 3. Modified Peterson olefination of 3 yields the unsaturated 4, which upon treatment with Pd/C and $H_2$ yields intermediate 5. Hydrolysis of the acetal, followed by AgO oxidation and esterification yields the diester 7. The diester is converted to the N-benzyl diamide by treatment with an excess of a 1:1 complex of benzyl amine and trimethyl aluminum, which upon treatment with 1 equivalent of para-toluenesulfonic acid in refluxing xylene yields the imide 8 as a mixture of cis- and trans-isomers, which are separated. Reduction of the purified imide isomers yields the cis- and trans-isomers of 9, which upon treatment with $H_2$/Pd yields the cis- and trans-isomers of the key intermediate 10. Alkylation with variously substituted alkyl halides yields the final products (11) described in this patent application.

Scheme II
Synthesis of 5-Alkoxy-2,3,4,4a,9,9a-hexahydro-1H-indeno[2,1-c]pyridines

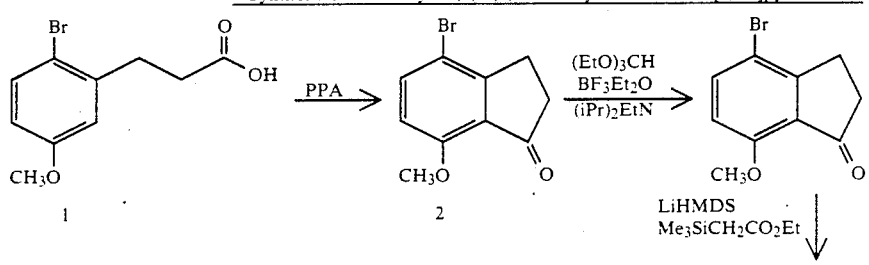

-continued
Scheme II
Synthesis of 5-Alkoxy-2,3,4,4a,9,9a-hexahydro-1H-indeno[2,1-c]pyridines

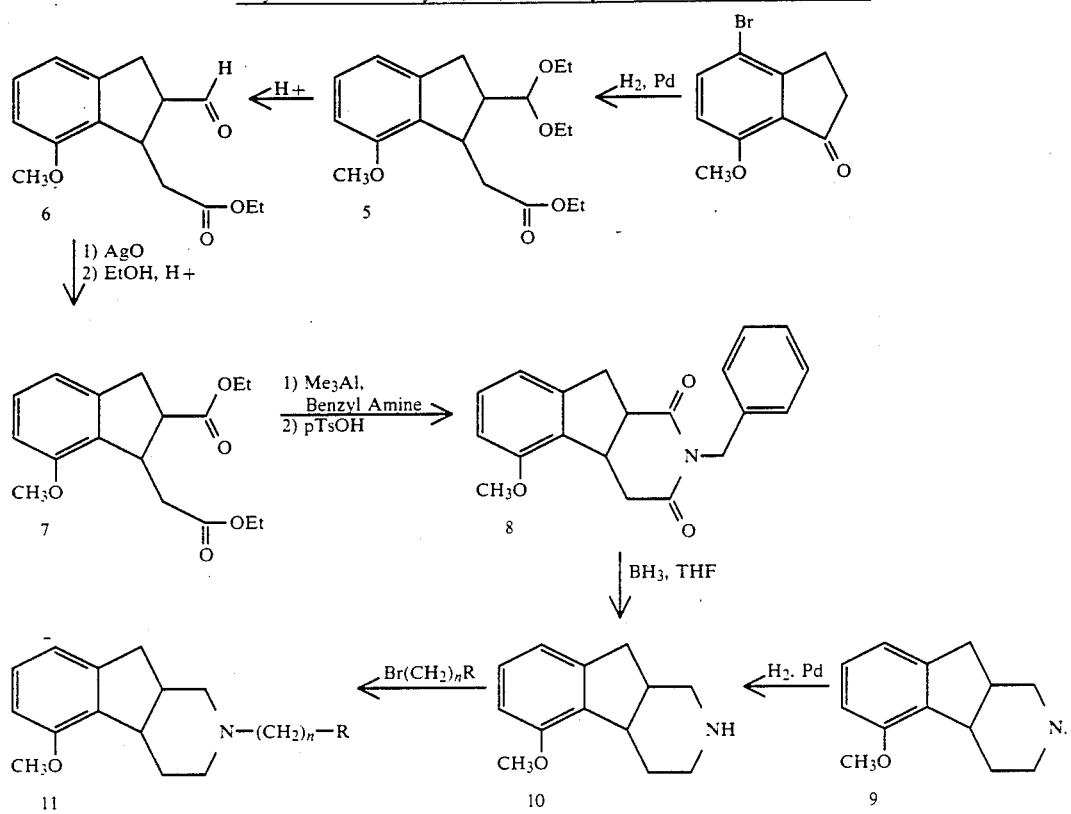

Referring now to Reaction Scheme III, the tetralone 1 is treated with 1.2 equivalents of TMSCN and a catalytic amount of LiCN in THF at 0° C., followed by dehydration with para-toluenesulfonic acid to yield the unsaturated nitrile 2. Conjugate addition of cyanide by treatment of the unsaturated nitrile with 1.2 equivalents of LiCN in the presence of 1.05 equivalents of acetic acid in DMF yields the dinitrile 3 as a mixture of cis- and trans-isomers. Hydrogenolysis of 3 with Pd/C and H₂ yields the dinitrile 4. Hydrogenation of the dinitrile employing a high load of Pd/C catalyst in methanol and aqueous HCl yields the isoindoline 5 as a mixture of cis- and trans-isomers, which are separated. Alkylation of 5 with variously substituted alkyl bromides in acetonitrile in the presence of ethyl diisopropyl amine yields the final products (6) described in this patent application.

Scheme III
Synthesis of 9-Alkoxy-2,3,3a,4,5,9b-hexahydro-1H-benz[3]isoindoles

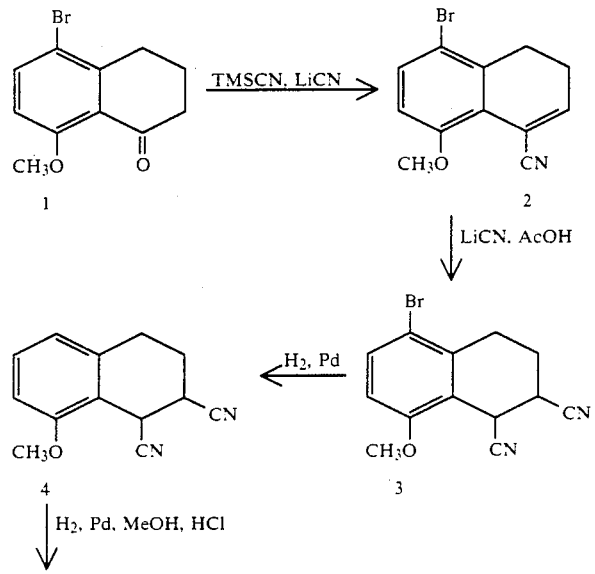

Scheme III
Synthesis of 9-Alkoxy-2,3,3a,4,5,9b-hexahydro-1H-benz[3]isoindoles

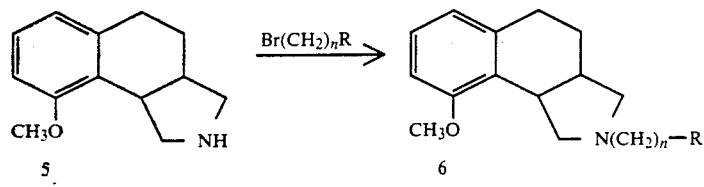

Referring to Reaction Scheme IIIa the ester 1 and diethyl oxalate are added to a suspension of potassium tert-butoxide in ether to yield the condensation product 2. Cyclization of the keto-diester 2 yields the dihydronaphthalene 3. Hydrogenation then yields the diester 4. The cis-diester derived from hydrogenation is epimerized to a 60:40 mixture of the trans:cis-diesters, from which the remaining cis-diester is removed by fractional crystallization. Reduction of the mother liquor with LiAlH$_4$ yields the trans-diol 5. The diol is then converted to the bis-mesylate 6, which upon treatment with a variety of amine substrates yields the trans-pyrrolidine 7. By employing an optically active amine such as (−)-α-methylbenzyl amine, the resulting diastereomeric pyrrolidines are isolated and, following debenzylation, the enantiomerically resolved pyrrolidines are obtained (R=H).

Scheme IIIa
Alternate Synthesis of 9-Alkoxy-2,3,3a,4,5,9b-Hexahydro-1H-Benz[e]isoindoles

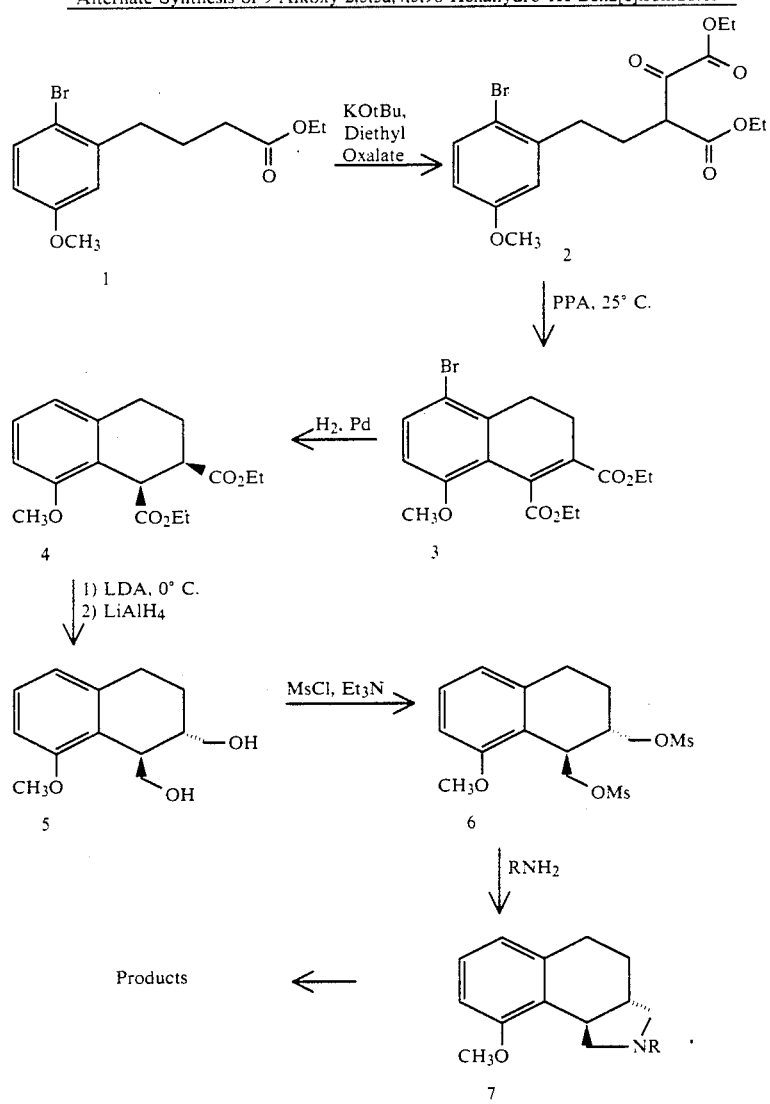

The following examples are provided to enable one skilled in the art to practice the present invention. These examples, however, are merely illustrative of the invention, and are not to be read as limiting the scope of the invention as it is defined by the appended claims.

EXAMPLE 1

Preparation of
2-Oxo-3-carboethoxy-4-(2-bromo-5-methoxyphenyl)-butanoic acid, ethyl ester Potassium t-butoxide (6.72 g) was suspended in 30 ml of anhydrous ether and cooled to 0° C. A solution of 14.35 g of ethyl 3-(2-bromo-5-methoxyphenyl)propionate and 10.95 g diethyl oxalate in 10 ml ether was added dropwise over 15 min. After 2 h at 25° C., the reaction was poured into 100 ml $H_2O$ and the aqueous layer was separated, acidified to pH 1 and extracted with ether. The ether layer was dried ($MgSO_4$) and the solvent was evaporated to yield 17.48 g of the desired product as a colorless oil (90%). NMR ($CDCl_3$) δ 1.20 (t, 3H), 1.35 (t, 3H), 3.32 (dd, 2H), 3.76 (s, 3H), 4.18 (q, 2H), 4.32 (q, 2H), 4.53 (t, 1H), 6.67 (dd, 1H), 6.80 (d, 1H), 7.40 (d, 1H).

EXAMPLE 2

Preparation of
7-Bromo-4-methoxy-1H-indene-2,3-dicarboxylic acid, diethyl ester

The ester from Example 1 (25.0 g) was added to 250 g polyphosphoric acid, and the reaction was stirred at 25° C. for 45 min. The reaction was poured into 1.5 kg ice/$H_2O$ and extracted with ether. The ether extracts were washed with 5% $NaHCO_3$ solution, brine, dried ($MgSO_4$) and evaporated to dryness. The resulting product was triturated with hot hexane, cooled, and filtered to yield 13.98 g of the desired product as a white solid, mp: 99-101° C. NMR ($CDCl_3$) δ 1.34 (t, 3H), 1.41 (t, 3H), 3.71 (s, 2H), 3.83 (s, 3H), 4.29 (q, 2H), 4.44 (q, 2H), 6.73 (d, 1H), 7.42 (d, 1H).

EXAMPLE 3

Preparation of
4-Methoxy-2,3-dihydro-1H-indene-2,3-dicarboxylic acid, diethyl ester The diester from Example 2 (19.39 g) was dissolved in 250 ml ethanol. To the solution was added 5.20 g of 10% Pd/$BaSO_4$ and 7.15 g $NaOAc.3H_2O$. The reaction was hydrogenated at 4 atm pressure. The catalyst was filtered and the solvent evaporated. The product was dissolved in ether, washed with 5% $NaHCO_3$, dried ($MgSO_4$), and the solvent was evaporated to yield 14.87 g of the desired product as a colorless oil. NMR ($CDCl_3$) δ 1.20 (t, 3H), 1.27 (t, 3H), 3.13 (dd, 1H), 3.48-3.56 (m, 2H), 3.82 (s, 3H), 3.95-4.22 (m, 4H), 4.39 (d, 1H), 6.70 (d, 1H), 6.87 (d, 1H), 7.21 (t, 1H).

EXAMPLE 4

Preparation of
2-Benzyl-8-methoxy-1,2,3,3a,8,8a-hexahydroindeno[1,2-c]pyrrole-1,3-dione Benzyl amine (8.02 g) was dissolved in 125 ml toluene.
To the solution was added 37.5 ml of a 2.0M solution of $Me_3Al$ in toluene. After 20 min., 7.30 g of the diester from example 3 was added. The reaction was heated at reflux for 2 hours, cooled to 0° C. and quenched by the dropwise addition of 15 ml $H_2O$. The reaction was poured in to 5% HCl solution and extracted with ethyl acetate. The organic extracts were washed with brine, dried ($MgSO_4$) and evaporated to dryness. The resulting product was dissolved in 400 ml xylene and 5.22 g pTsOH.$H_2O$ and heated at reflux for 18 h. The solvent was evaporated and the product was recrystallized from methanol to yield 6.10 g of the desired product as a white solid, mp: 170-2° C. NMR ($CDCl_3$) δ 3.37 (dd, 2H), 3.63 (m, 1H), 3.91 (s, 3H), 4.52 (d, 1H), 4.60 (dd, 2H), 6.77 (d, 1H), 6.73 (d, 1H), 7.21-7.37 (m, 6H).

EXAMPLE 5

Preparation of
2-Benzyl-8-methoxy-1,2,3,3a,8,8a-hexahydroindeno[1,2-c]pyrrole hydrochloride The product from Example 4 (5.76 g) was dissolved in 200 ml tetrahydrofuran (THF) and to the solution was added 2.88 g $LiAlH_4$. The reaction was stirred at reflux for 3 h, and then cooled to 25° C. and quenched by the addition of 2.9 ml $H_2O$, 2.9 ml 15% NaOH, 8.7 ml $H_2O$. The reaction was filtered and the solvent evaporated to dryness. The product was dissolved in diethyl ether and treated with an ethereal solution of HCl, evaporated to dryness, and then recrystallized from $CH_2Cl_2$/EtOAc to yield 4.90 g of the desired product as a white solid, mp: 222-3° C. NMR ($d_6$DMSO) δ 2.7-3.9 (m, 8H), 3.77 (s, 3H), 4.33 (dd, 2H), 6.78, (d, 2H), 6.83 (d, 2H), 7.23 (t, 1H), 7.40-7.60 (m, 5H).

EXAMPLE 6

Preparation of
8-Methoxy-1,2,3,3a,8,8a-hexahydro-indeno[1,2-c]pyrrole hydrochloride The product from Example 5 (4.90 g) was hydrogenated with 2.45 g 20% Pd/C in 200 ml methanol at 3 atm, affording 3.17 g of the desired product, mp: 208-209° C. NMR ($d_6$ DMSO/$D_2O$) δ 2.83 (m, 2H), 3.14-3.29 (m, 3H), 3.46 (dd, 1H), 3.55 (dd, 1H), 3.80 (s, 3H), 3.95 (m, 1H), 6.85 (d, 2H), 7.25 (t, 1H).

Analysis, theoretical (¼$H_2O$): C, 62.61; H, 7.22; N, 6.08. Found: C, 62.24; H, 7.00; N, 5.87.

EXAMPLE 7

Preparation of
2-(4-(3,3-tetramethylene)glutarimidyl)butyl-8-methoxy-1,2,3,3a,8,8a-hexahydro-indeno[1,2-c]pyrrole hydrochloride The product from Example 6 (0.902 g) was combined with 1.33 g 1-bromo-4-(3,3-tetramethyleneglutarimidyl)-butane and 2.1 ml diisopropyl ethyl amine in 10 ml acetonitrile. After 18 h at reflux, the reaction was quenched in aqueous 5% $NaHCO_3$ solution and extracted with diethyl ether. The ether extracts were dried ($K_2CO_3$) and evaporated. The resulting oil was treated with ethereal HCl, and the resulting hydrochloride salt was recrystallized from EtOAc/ether to yield 1.15 g of a white solid, mp: 117-22° C. NMR ($d_6$ DMSO) δ 1.40 (m, 6H), 1.53 (m, 6H), 2.62 (s, 4H), 2.70-3.50 (m, 10H), 3.62 (t, 2H), 3.80 (s, 3H), 6.83 (d, 2H), 7.23 (t, 1H).

Analysis, theoretical (with 1 $H_2O$): C, 64.57; H, 8.02; N, 6.02. Found: C, 64.96; H, 7.66; N, 6.01.

EXAMPLE 8

Preparation of
2-(4-(3,3-tetramethylene)glutarimidyl)butyl-5-chloro-8-methoxy-1,2,3,3a,8,8a-hexahydroindeno[1,2-c]pyrrole hydrochloride The product from Example 7 (0.446 g) was dissolved in 5 ml methylene chloride and 1 ml acetic acid. The solution was cooled to 0° C. and a solution of Cl₂ in acetic acid (1 ml of a 1.0M solution) was added. After 15 min, the solvent was evaporated, and the resulting product was recrystallized from ethyl acetate and ether to yield 0.410 g of a white solid, mp: 157–60° C. NMR (d₆ DMSO) δ 1.40 (m, 6H), 1.60 (m, 6H), 2.60 (s, 4H), 2.60–3.40 (m, 12H), 3.60 (t, 2H), 3.80 (s, 3H), 3.97 (m, 2H), 6.90 (d, 1H), 7.30 (d, 1H).

Analysis, theoretical: C, 62.37; H, 7.12; N, 5.82. Found: C, 62.77; H, 7.23; N, 5.73.

EXAMPLE 9

Preparation of 8-Methoxy-2-propyl-1,2,3,3a,8,8a-hexahydroindeno[1,2-c]pyrrole hydrochloride The product from Example 6 (1.00 g) was dissolved in 100 ml ethanol. To the reaction was added 2 ml propionaldehyde and 100 mg 10% Pt/C. The reaction was hydrogenated for 4 h at 3 atm, filtered, and evaporated. The resulting product was recrystallized from ethanol and ether to yield 0.825 g of the desired product, mp: 161–3° C. NMR (d₆ DMSO) δ 0.88 (t, 3H), 1.62 (m, 2H), 2.55–3.60 (m, 8H), 3.80 (s, 3H), 3.80–4.08 (m, 2H), 6.82 (d, 2H), 7.23 (t, 1H).

Analysis, theoretical: C, 67.28; H, 8.28; N, 5.15. Found: C, 66.73; H, 8.26; N, 5.15.

EXAMPLE 10

Preparation of 8-Hydroxy-2-propyl-1,2,3,3a,8,8a-hexahydroindeno[1,2-c]pyrrole hydrobromide The product from Example 9 (0.490 g) was dissolved in 25 ml methylene chloride and cooled to −78° C. To the reaction was added 0.69 ml BBr₃. The reaction was warmed to 0° C. for 4 h and then cooled to −78° C. The reaction was quenched by the addition of 5 ml methanol and the solvent was evaporated. The resulting solid was recrystallized from ethanol and ether to yield 0.470 g white solid, mp: 187–9° C. NMR (d₆ DMSO) δ 0.88 (t, 3H), 1.65 (m, 2H), 2.60–4.10 (m, 10H), 6.65 (d, 1H), 6.70 (d, 1H), 7.05 (t, 1H).

Analysis, theoretical: C, 56.39; H, 6.76; N, 4.70. Found: C, 56.42; N, 6.53; N, 4.65.

EXAMPLE 11

Preparation of 8-Hydroxy-1,2,3,3a,8,8a-hexahydro-indeno[1,2-c]pyrrole hydrobromide The product from Example 6 (0.226 g) was treated as described in Example 10 to yield 0.204 g of a white solid, mp: 221–2° C. NMR (d₆ DMSO) δ 2.83 (m, 2H), 3.10–3.60 (m, 5H), 3.92 (m, 1H), 6.67 (d, 1H), 6.70 (d, 1H), 7.07 (t, 1H).

Analysis, theoretical ($\frac{1}{4}$ H₂O): C, 50.69; H, 5.61; N, 5.37. Found: C, 50.61; H, 5.45; N, 5.22.

EXAMPLE 12

Preparation of 8-Methoxy-2-methyl-1,2,3,3a,8,8a-hexahydroindeno[1,2-c]pyrrole hydrochloride The product from Example 6 (0 600 g) was dissolved in 15 ml methanol and 8 ml 37% aqueous formaldehyde. The solution was stirred with 0.80 g NaBH₃CN for 18 h. The reaction was quenched in H₂O, basified to pH 10, and extracted with ether. The ether extracts were dried, treated with ethereal HCl, and evaporated. The resulting white solid was recrystallized from ethanol and ether to yield 0.355 g of a white solid, mp: 184–5° C. NMR (d₆ DMSO) δ 2.75 (s, 3H), 2.55–4.05 (m, 8H), 3.80 (s, 3H), 6.82 (d, 2H), 7.22 (t, 1H).

Analysis, theoretical ($\frac{1}{8}$ H₂O): C, 64.53; H, 7.60; N, 5.78. Found: C, 64.48; H, 7.44; N, 5.70.

EXAMPLE 13

Preparation of 8-Methoxy-2-ethyl-1,2,3,3a,8,8a-hexahydroindeno[1,2-c]pyrrole hydrochloride The product from Example 6 (0.580 g) was dissolved in 50 ml ethanol. To the reaction was added 2 ml acetaldehyde and 100 mg 10% Pt/C. The reaction was hydrogenated for 4 h at 3 atm, filtered, and evaporated. The resulting product was recrystallized from ethanol and ether to yield 0.501 g of the desired product, mp: 161–3° C. NMR (d₆ DMSO) δ 1.30 (m, 3H), 2.55–3.60 (m, 8H), 3.80 (s, 3H), 3.80–4.08 (m, 2H), 6.82 (m, 2H), 7.22 (t, 1H).

Analysis, theoretical: C, 66.26; H, 7.94; N, 5.52. Found: C, 65.74; H, 7.86; N, 5.31.

EXAMPLE 14

Preparation of 8-Hydroxy-2-methyl-1,2,3,3a,8,8a-hexahydroindeno[1,2-c]pyrrole hydrobromide The product from Example 12 (0.479 g) was treated as described in Example 10 to yield 0.465 g of the desired product, mp: 213–15° C. NMR (d₆ DMSO) δ 2.60–3.50 (m, 5H), 3.35 (s, 3H), 3.60–4.10 (m, 3H), 6.65 (m, 2H), 7.07 (t, 1H).

Analysis, theoretical ($\frac{1}{4}$ H₂O): C, 52.47; H, 6.05; N, 5.10. Found: C, 52.61; H, 5.78; N, 5.03.

EXAMPLE 15

Preparation of 8-Hydroxy-2-ethyl-1,2,3,3a,8,8a-hexahydroindeno[1,2-c]pyrrole hydrobromide The product from Example 13 (0.350 g) was treated as described in Example 10 to yield 0.358 g of the desired product, mp: 168–70° - C. NMR (d₆ DMSO) δ 1.20 (t, 3H), 2.50–4.10 (m, 10H), 6.66 (d, 1H), 6.69 (d, 1H), 7.07 (t, 1H).

Analysis, theoretical ($\frac{1}{4}$ H₂O): C, 54.09; H, 6.46; N, 4.85. Found: C, 54.16; H, 6.27; N, 4.66.

EXAMPLE 16

Preparation of 8-Methoxy-2-cyanomethyl-1,2,3,3a,8,8a-hexahydroindeno[1,2-c]pyrrole The product from Example 6 (0.895 g) was dissolved in 4 ml acetonitrile and 4 ml diisopropyl ethyl amine. 0.270 ml chloroacetonitrile was added and the reaction was stirred at 60° C. for 18 h. The reaction was quenched in 5% aqueous NaOH and extracted with methylene chloride, dried (K₂CO₃), and evaporated to yield 0.937 g of the desired product as a white solid. NMR (CDCl₃) δ 2.56 (dd, 1H), 2.81 (m, 1H), 2.89 (m, 2H), 3.02 (t, 1H), 3.12 (m, 1H), 3.29 (t, 1H), 3.62 (s, 2H), 3.81 (s, 3H), 3.89 (m, 1H), 6.66 (d, 1H), 6.78 (d, 1H), 7.17 (t, 1H).

EXAMPLE 17

Preparation of 8-Methoxy-2-(2-aminomethyl-1,2,3,3a,8,8a-hexahydroindeno[1,2-c]pyrrole The product from Example 16 (1.00 g) was dissolved in 90 ml methanol and 10 ml anhydrous ammonia. 0.100 g 5%Rh/Al$_2$O$_3$ was added and the reaction was hydrogenated at 4 atm for 4 h. The reaction was filtered and the solvent removed to yield 0.97 g of the desired product as a colorless oil. NMR (CDCl$_3$) δ 2.20–2.61 (m, 3H), 2.66–3.45 (m, 8H), 3.82 (s, 3H), 3.89 (m, 1H), 6.67 (d, 1H), 6.78 (d, 1H), 7.14 (t, 1H).

EXAMPLE 18

Preparation of 8-Methoxy-2-(2-4-fluorobenzamido)ethyl-1,2,3,3a,8,8a-hexahydroindeno[1,2-c]pyrrole hydrochloride The product from Example 17 (0.95 g) was dissolved in 50 ml methylene chloride and 1.5 ml triethyl amine. The solution was cooled to −20° C. and 0.59 ml p-fluorobenzoyl chloride was added. After 30 min, the reaction was quenched in 5% NaHCO$_3$ and extracted with ethyl acetate. The organic extracts were dried (Na$_2$SO$_4$), evaporated, and the product was dissolved in ether and treated with ethereal HCl and then evaporated to dryness. The resulting product was recrystallized from ethyl acetate and ether to yield 0.772 g of the desired product as a white solid, mp: 197–8° C. NMR (d$_6$ DMSO) δ 2.60–3.10 (m, 3H), 3.00–3.50 (m, 4H), 3.59 (m, 2H), 3.78 (s, 3H), 3.82–4.22 (m, 3H), 6.83 (d, 1H), 6.87 (d, 1H), 7.23 (t, 1H), 7.34 (m, 2H), 8.00 (m, 2H).

Analysis, theoretical: C, 64.53; H, 6.19; N, 7.17. Found: C, 64.40; H, 6.20; N, 7.07.

EXAMPLE 19

Preparation of 8-Hydroxy-2-(2-(4-fluorobenzamido)ethyl-1,2,3,3a,8,8a-hexahydroindeno[1,2-c]pyrrole hydrobromide The product from Example 18 (0.323 g) was treated as described in Example 10 to yield 0.347 g of the desired product as a white solid, mp: 144–7° C. NMR (d$_6$ DMSO) δ 2.70–4.40 (m, 12H), 6.68 (m, 2H), 7.07 (t, 1H), 7.35 (m, 2H), 7.97 (m, 2H).

Analysis, theoretical (½ H$_2$O): C, 55.82; H, 5.39; N, 6.51. Found: C, 55.68; H, 5.20; N, 6.45.

EXAMPLE 20

Preparation of 2-(4-(3,3-tetramethylene)glutarimidyl)butyl-8-hydroxy-1,2,3,3a,8,8a-hexahydro-indeno[1,2-c]pyrrole hydrobromide The product from Example 7 (0.446 g) was treated as described in Example 10 to yield 0.359 g of the desired product as a white solid, mp: 167–9° C. NMR (d$_6$ DMSO) δ 1.40 (m, 6H), 1.62 (m, 6H), 2.63 (s, 4H), 2.70–3.45 (m, 8H), 3.61 (t, 2H), 3.70–4.10 (m, 2H), 6.65 (m, 2H), 7.03 (t, 1H).

Analysis, theoretical (½ H$_2$O): C, 65.22; H, 7.75; N, 6.34. Found: C, 65.41; H, 7.45; N, 6.34.

EXAMPLE 21

Preparation of 8-Methoxy-2-(4-(2-(1,2-benzisothiazolin-3-one-1,1-dioxide))butyl)1,2,3,3a,8,8a-hexahydro-indeno[1,2-c]pyrrole hydrochloride The product from Example 6 (0.902 g) was dissolved in 10 ml acetonitrile and 2 ml diisopropyl ethyl amine. To the reaction was added 1.59 g 4-bromobutyl-2-(1,2-benzisothiazolin-3-one-1,1-dioxide, and the reaction was heated at reflux for 4 h. The reaction was quenched in 5% NaHCO$_3$, extracted with ether, dried (K$_2$CO$_3$), and evaporated to dryness. The product, after chromatography, was treated with ethereal HCl, and then recrystallized from ethanol and ether to yield 1.08 g of the desired product as a white solid, mp: 175–8° C. NMR (d$_6$ DMSO) δ 2.50–4.10 (m, 16H), 3.80 (s, 3H), 6.82 (m, 2H), 7.22 (t, 1H), 8.07 (m, 3H), 8.31 (m, 1H).

Analysis, theoretical: C, 59.67; H, 5.88; N, 6.05. Found: C, 59.47; H, 5.98; N, 6.01.

EXAMPLE 22

Preparation of 8-Hydroxy-2-(4-(2-(1,2-benzisothiazolin-3-one-1,1-dioxide))butyl)1,2,3,3a,8,8a-hexahydro-indeno[1,2-c]pyrrole hydrochloride The product from Example 21 (0.462 g) was treated as described in Example 10 to yield 0.309 g of the desired product as a white solid, mp: 218–20° C. NMR (d$_6$ DMSO) δ 2.55–3.50 (m, 10H), 3.60–4.15 (m, 6H), 6.68 (m, 2H), 7.05 (t, 1H), 8.10 (m, 3H), 8.32 (d, 1H).

Analysis, theoretical: C, 53.55; H, 5.11; N, 5.68. Found: C, 53.11; H, 5.01; N, 5.61.

EXAMPLE 23

Preparation of 2-(4-(3,3-dimethyl)glutarimidyl)butyl-8-methoxy-1,2,3,3a,8,8a-hexahydro-indeno[1,2-c]pyrrole hydrochloride The product from Example 6 (0.60 g) was combined with 0.82 g. 1-bromo-4-(3,3-dimethylglutarimidyl)-butane and 1.4 ml diisopropyl ethyl amine in 10 ml acetonitrile. After 18 h at reflux, the reaction was quenched in aqueous 5% NaHCO$_3$ solution and extracted with diethyl ether. The organic layer was washed with brine, dried (K$_2$CO$_3$) and evaporated. The resulting oil was treated with ethereal HCl, and the resulting hydrochloride salt was recrystallized from EtOAc/ether to yield 0.58 g of a white solid, mp: 143–146° C. NMR (d$_6$ DMSO) δ 0.95 (s, 5H), 1.40 (q, 2H), 1.60 (m, 2H), 2.05 (s, 3H), 2.60–3.20 (m, 8H), 3.35 (s, 4H), 3.65 (t, 2H), 3.80 (s, 3H), 6.85 (d, 2H), 7.25 (t, 1H).

Analysis, theoretical (with ½ H$_2$O): C, 64.93; H, 7.94; N, 6.58. Found: C, 64.62; H, 7.79; N, 6.52.

EXAMPLE 24

Preparation of 8-Methoxy-2-(4-(2-phthalimido)butyl)-1,2,3,3a,8,8a-hexahydroindeno[1,2-c]pyrrole hydrochloride The product from Example 6 (0.60 g) was combined with 0.84 g. 1-bromo-4-(phthalimidyl)-butane and 1.4 ml diisopropyl ethyl amine in 10 ml acetonitrile. After 18 h at reflux, the reaction was quenched in aqueous 5% NaHCO$_3$ solution and extracted with diethyl ether. The organic layer was washed with brine, dried (K$_2$CO$_3$)

and evaporated. The resulting oil was treated with ethereal HCl, and the resulting hydrochloride salt was recrystallized from EtOAc/ether to yield 0.56 g of a white solid, mp: 196–198° C. NMR (d$_6$ DMSO) δ 1.65 (m, 4H), 2.60–3.20 (m, 6H), 3.60 (m, 2H), 3.80 (s, 3H), 3.90 (m, 2H), 6.80 (m, 2H), 7.20 (m, 1H), 7.75 (m, 4H).

Analysis, theoretical: C, 67.52; H, 6.37; N, 6.56. Found: C, 67.39; H, 6.47; N, 6.46.

EXAMPLE 25

Preparation of
8-Hydroxy-2-(4-(2-phthalimido)butyl)-1,2,3,3a,8,8a-hexahydroindeno[1,2-c]pyrrole hydrobromide The resultant of Example 24 (0.53 g) was treated as described in Example 10 to yield 0.47 g of the desired product, mp: 185–190° C. NMR (CDCl$_3$) δ 1.20 (t, 1H), 1.25–2.00 (m, 5H), 2.50–3.20 (m, 6H), 3.50 (q, 1H), 3.60–4.50 (m, 5H), 6.75 (d, 1H), 6.90 (d, 1H) 7.10 (t, 1H), 7.60–7.90 (m, 4H).

Analysis, theoretical (with ½ H$_2$O): C, 59.23; H, 5.62; N, 6.01; Found: C, 58.88; H, 5.55; N, 5.53.

EXAMPLE 26

Preparation of
2-(3-(3,3-tetramethylene)glutarimidyl)propyl-8-methoxy-1,2,3,3a,8,8a-hexahydro-indeno[1,2-c]pyrrole hydrochloride The resultant of Example 6 (1.00 g) was dissolved in 20 ml of acetonitrile and 2.3 ml diisopropyl ethyl amine. To the reaction was added 1.40 g 1-bromo-3-(3,3-tetramethyleneglutarimidyl)-propane, and the reaction was heated at reflux for 18 h. The reaction was quenched in aqueous 5% NaHCO$_3$ solution, extracted with ether, dried (K$_2$CO$_3$) and evaporated. The resulting oil was treated with ethereal HCl, and the resulting hydrochloride salt was recrystallized from methylene chloride/ether to yield 0.53 g of a white solid, mp: 170–174° C. NMR (CDCl$_3$) δ 1.50 (m, 4H), 1.70 (m, 4H), 2.10 (m, 2H), 2.40 (q, 1H), 2.60–3.00 (m, 4H), 3.20 (q, 1H), 3.60 (m, 1H), 3.80–3.90 (m, 6H), 4.10–4.30 (m, 3H), 6.80 (q, 2H), 7.25 (t, 1H).

Analysis, theoretical (with ¼ H$_2$O): C, 65.89; H, 7.60; N, 6.40. Found: C, 65.80; H, 7.76; N, 6.24.

EXAMPLE 27

Preparation of
2-(3-(3,3-tetramethylene)glutarimidyl)propyl-8-hydroxy-1,2,3,3a,8,8a-hexahydro-indeno[1,2-c]pyrrole hydrobromide The product from Example 26 (0.30 g) was treated as described in Example 10 to yield 0.27 g of the desired product, mp: 152–6° C. NMR (CDCl$_3$) δ 1.20 (t, 1H), 1.50 (m, 4H), 1.70 (m, 4H), 2.10 (m, 2H), 2.60 (s, 4H), 2.80 (d, 1H), 3.00 (m, 3H), 3.20 (q, 1H), 3.50 (q, 1H), 3.80 (t, 2H), 3.90 (m, 1H), 4.20 (m, 1H), 4.40 (m, 1H), 6.70–6.90 (q, 2H), 7.10 (t, 3H).

Analysis, theoretical (with ½ H$_2$O): C, 58.47; H, 6.83; N, 5.93. Found: C, 58.48; H, 6.86; N, 5.79.

EXAMPLE 28

Preparation of
2-(5-(3,3-tetramethylene)glutarimidyl)pentyl-8-methoxy-1,2,3,3a,8,8a-hexahydro-indeno[1,2-c]pyrrole hydrochloride The product from Example 6 (1.05 g) was combined with 1.66 g. 1-bromo-5-(3,3-tetramethyleneglutarimidyl)-pentane and 2.4 ml diisopropyl ethyl amine in 50 ml acetonitrile. After 18 h at reflux, the reaction was quenched in aqueous 5% NaHCO$_3$ solution and extracted with diethyl ether. The organic layer was washed with brine, dried (K$_2$CO$_3$) and evaporated. The resulting oil was treated with ethereal HCl, and the resulting hydrochloride salt was lyophilized to yield a white amorphous solid. NMR (CDCl$_3$) δ 1.30–1.90 (m, 15H), 2.40 (m, 1H), 2.60 (s, 1H), 2.70–2.90 (m, 4H). 3.20 (s, 3H), 3.60 (m, 1H), 3.70 (t, 2H), 3.80 (s, 3H), 4.10–4.30 (m, 2H), 6.70 (d, 1H), 6.85 (d, 1H), 7.25 (t, 1H).

Analysis, theoretical (with 2 moles H$_2$O): C, 62.82; H, 8.31; N, 5.64. Found: C, 62.79; H, 7.76; N, 5.48.

EXAMPLE 29

Preparation of
2-(4-(3,3-tetramethylene)glutarimidyl)-cis-but-2-enyl-8-methoxy-1,2,3,3a,8,8a-hexahydro-indeno[1,2-c]pyrrole hydrochloride The product from Example 6 (1.05 g) was treated with 1.25 g cis-1-bromo-4-(3,3-tetramethyleneglutarimidyl)-2-butene as described in Example 28 to yield 0.75 g of a white amorphous solid. NMR (CDCl$_3$) δ 1.50 (m, 4H), 1.70 (m, 4H), 2.55 (s, 4H), 2.60–3.60 (m, 6H), 3.80 (m, 5H), 4.10–4.30 (m, 4H), 5.70–6.00 (m, 2H), 6.75–6.85 (q, 2H), 7.25 (t, 1H).

Analysis, theoretical (with ¼ H$_2$O): C, 66.80; H, 7.51; N, 6.23. Found: C, 66.50; H, 7.44; N, 6.18.

EXAMPLE 30

Preparation of
2-(4-(3,3-tetramethylene)glutarimidyl)-trans-but-2-enyl-8-methoxy-1,2,3,3a,8,8a-hexahydro-indeno[1,2-c]pyrrole hydrochloride The product from Example 6 (0.80 g) was combined with 1.17 g trans-1-bromo-4-(3,3-tetramethyleneglutarimidyl)-2-butene and 1.8 ml diisopropyl ethyl amine in 50 ml acetonitrile. After 18 h at reflux, the reaction was quenched in 5% NaHCO$_3$ and extracted with ether. The organic layer was washed with brine, dried (K$_2$CO$_3$) and evaporated. The resulting oil was treated with ethereal HCl, and the resulting hydrochloride salt was recrystallized from methylene chloride/ether to yield 0.46 g of a white solid, mp: 155–157° C. NMR (CDCl$_3$) δ 1.50 (m, 4H), 1.70 (m, 4H), 2.40 (q, 1H), 2.70 (s, 4H), 2.80–3.75 (m, 8H), 4.10 (m, 2H), 4.40 (m, 2H), 5.70–5.90 (m, 2H), 6.70–6.80 (q, 2H), 7.25 (t, 1H).

Analytical, theoretical (with ¼ H$_2$O): C, 66.79; H, 7.40; N, 6.23. Found: C, 67.05; H, 7.51; N, 6.06.

EXAMPLE 31

Preparation of
2-(S-1,4-benzodioxanyl-2-methyl)-8-methoxy-1,2,3,3a,8,8a-hexahydro-indeno[1,2-c]pyrrole hydrochloride The product from Example 6 (0.300 g) was dissolved in 10 ml acetonitrile and 1.0 ml diisopropyl ethyl amine. To the solution was added 0.600 g R-2-tosyloxymethyl-1,4-benzodioxan, and the reaction was heated at reflux for 18 h. The product, after chromatographic purification, was converted to its hydrochloride salt, mp: 196–8° C. NMR (d$_6$ DMSO) δ 2.70–3.95 (m, 10H), 3.80 (s, 3H), 4.05 (m, 1H), 4.27 (m, 1H), 4.75 (m, 1H), 6.88 (m, 6H), 7.23 (m, 1H).

Analysis, theoretical (½.H$_2$O): C, 65.88; H, 6.58; N, 3.66. Found: C, 65.40; H, 6.44; N, 3.54.

EXAMPLE 32

Preparation of
2-(R-1,4-benzodioxanyl-2-methyl)-8-methoxy-1,2,3,3a,8,8a-hexahydro-indeno[1,2-c]pyrrole hydrochloride The product from Example 6 (0.300 g) was treated with 0.600 g 2-S-tosyloxymethyl-1,4-benzodioxan as described in Example 31 to yield 0.340 g of the desired product as a white solid, mp: 190-2° C. NMR (d$_6$ DMSO) δ 2.70-3.70 (m, 8H), 3.80 (s, 3H), 3.88-4.18 (m, 3H), 4.30 (m, 1H), 4.79 (m, 1H), 6.80-7.50 (m, 7H).

Analysis, theoretical (¼.H20): C, 65.88; H, 6.58; N, 3.66. Found: C, 65.27; H, 6.33; N, 3.35.

EXAMPLE 33

Preparation of
8-methoxy-2-(2-phenyl)ethyl-1,2,3,3a,8,8a-hexahydro-indeno[1,2-c]pyrrole hydrochloride The product from Example 6 (0.870 g) was converted to its free base and treated with 0.654 g phenylacetic acid and 0.912 g dicyclohexylcarbodiimide in tetrahydrofuran. The resulting amide was treated with 0.900 g LiAlH$_4$ in 30 ml tetrahydrofuran at 25° C. for 3 h, quenched by the addition of H$_2$O and 15% NaOH, and then converted to its HCl salt to yield 0.570 g of a white solid, mp: 186-8° C. NMR (d$_6$ DMSO) δ 2.70-3.20 (m, 9H), 3.80 (s, 3H), 3.81-4.11 (m, 3H), 6.83 (m, 2H), 7.29 (m, 6H).

Analysis, theoretical (¼.H$_2$O): C, 71.84; H, 7.39; N, 4.19. Found: C, 72.19; H, 7.24; N, 4.11.

EXAMPLE 34

Preparation of
4-Bromo-7-methoxy-2,3-dihydro-1H-inden-1-one

Polyphosphoric acid (600 g) was heated to 90° C. and 30 g 2-bromo-5-methoxyphenyl propionic acid was added over 25 min. The reaction was stirred an additional 10 min and then quenched by addition to 2 kg ice. The reaction mixture was extracted with methylene chloride, and the organic extracts were washed with 5% NaHCO$_3$, brine, dried (MgSO$_4$), and evaporated. The product was recrystallized from methanol to yield 15.10 g of a light yellow solid, mp: 125-8° C. NMR (CDCl$_3$) δ 2.70 (m, 2H), 3.00 (m, 2H), 3.95 (s, 3H), 6.73 (d, 1H), 7.66 (d, 1H).

EXAMPLE 35

Preparation of
4-Bromo-7-methoxy-1-oxo-2,3-dihydro-1H-indene-2-carboxaldehyde diethyl acetal Triethyl orthoformate (16.5 ml) was cooled to −30° C. and 15.0 ml BF$_3$.Et$_2$O in 50 ml methylene chloride was added. The reaction was warmed to 0° C. for 15 min, and then cooled to −78° C. To the reaction was added 12.05 g of the product from Example 34 in 50 ml methylene chloride, followed by dropwise addition of 19.4 ml diisopropyl ethyl amine. The reaction was then warmed to −15° C. for 2 h, then quenched in 5% NaHCO$_3$ solution and extracted with methylene chloride. The organic extracts were washed with brine, dried (MgSO$_4$), and the solvent removed. The crude product was triturated with cold hexane, and the crystalline product collected to yield 14.60 g of a white solid, mp: 76-8° C. NMR (CDCl$_3$) δ 1.05 (t, 3H), 1.27 (t, 3H), 3.03 (m, 2H), 3.30 (m, 1H), 3.43-3.80 (m, 4H), 3.95 (s, 3H), 5.00 (d, 1H), 6.71 (d, 1H), 7.63 (d, 1H).

EXAMPLE 36

Preparation of
4-Bromo-7-Methoxy-2,3-dihydro-1H-1-carboethoxymethylene-2-carboxaldehyde, diethyl acetal Ethyl trimethylsilyl acetate (1.12 g) was dissolved in 10 ml tetrahydrofuran and cooled to −78° C. To the solution was added 7.0 ml lithium hexamethyldisilazide (1.0 M in THF). After 20 min, 1.71 g of the product from Example 35 in 10 ml THF was added. The reaction was stirred at −78° C. for 2.5 h and then warmed to 25° C., and then quenched in H$_2$O and extracted with ether. The organic extracts were washed with brine, dried (MgSO$_4$), and evaporated to yield 1.96 g of the desired product as a white solid, mp: 73-5° C. NMR (CDCl$_3$) d 0.85 (t, 3H), 1.37 (t, 3H), 1.42 (t, 3H), 2.90 (dd, 1H), 3.27 (m, 2H), 3.52-3.81 (m, 4H), 3.90 (s, 3H), 4.21 (q, 2H), 4.78 (d, 1H), 6.62 (d, 1H), 6.90 (d, 1H), 7.39 (d, 1H).

EXAMPLE 37

Preparation of
7-Methoxy-2,3-dihydro-1H-indene-2-carboxaldehyde, diethyl acetal-1-acetic acid, ethyl ester The product from Example 36 (10.0 g) was dissolved in ethanol (250 ml) and 3.63 g NaOAc.H$_2$O was added, followed by 2.0 g 10% Pd/C. The reaction was hydrogenated at 4 atm for 4 h, filtered, and the solvent removed. The product was dissolved in ether, washed with 5% NaHCO$_3$ solution, dried (MgSO$_4$), and the solvent evaporated to yield 7.80 g of the desired product as a colorless oil. NMR (CDCl$_3$) δ 1.20 (m, 9H), 2.49 (dd, 1H), 2.70 (dd, 1H), 2.85 (m, 3H), 3.52 (q, 2H), 3.70 (m, 3H), 3.80 (s, 3H), 4.03 (q, 2H), 4.73 (d, 1H), 6.67 (d, 1H), 6.80 (d, 1H), 7.13 (t, 1H).

EXAMPLE 38

Preparation of
7-Methoxy-2,3-dihydro-1H-indene-2carboxaldehyde-1-acetic acid, ethyl ester The product from Example 37 (2.90 g) was dissolved in 40 ml THF and 8 ml 6N aq. HCl. After 45 min and 25° C., the reaction was quenched in 5% NaHCO$_3$ solution and extracted with ether. The ether extracts were dried (MgSO$_4$), and evaporated to dryness to yield 1.98 g of the desired product as a mixture of cis- and trans-isomers. NMR (CDCl$_3$) δ 1.75 (m, 3H), 2.48 (m, 1H), 2.90 (m, 1H), 3.15 (m, 2H), 3.70 (m, 1H), 3.80 (s, 3H), 4.15 (m, 3H), 6.68 (m, 1H), 6.82 (m, 1H), 7.17 (m 1H), 9.80 and 9.90 (two d, 1H).

EXAMPLE 39

Preparation of
7-Methoxy-2,3-dihydro-1H-indene-2carboxylic acid-1-acetic acid, diethyl ester The product from Example 38 (2.09 g) was dissolved in 35 ml ethanol. To the solution was added 2.93 g AgNO$_3$ in 5 ml H$_2$O, followed by 2.40 g KOH in 35 ml H$_2$O. After 40 min., the reaction was filtered and the aqueous solution was extracted with ether. The aqueous solution was acidified to pH 1 and extracted with methylene chloride; and the organic phase was washed with brine, dried (MgSO$_4$), and evaporated. The residue was dissolved in absolute ethanol and 0.5 ml 96% H$_2$SO$_4$ was added. The reaction was heated at reflux for 2 h, quenched in 5% NaHCO$_3$, and extracted with ether. The organic extracts were dried (MgSO$_4$) and evaporated to yield 1.99 g of the desired product as a colorless oil. NMR (CDCl$_3$) δ 1.25 (m, 6H), 2.50 (m, 2H), 3.25 (m, 4H), 3.80 (s, 3H), 4.12 (m, 4H), 6.67 (d, 1H), 6.80 (d, 1H), 7.17 (t, 1H).

EXAMPLE 40

Preparation of cis- and trans-2-benzyl-5-methoxy-2,3,4,4a,9,9a-hexahydro-1H-indeno[2,1-c]pyridine-1,3-dione Benzyl amine (4.82 g) was dissolved in 60 ml toluene. To the solution was added 22.5 ml of 2.0 M Me$_3$Al in toluene. After 1 h at 25° C., 4.59 g of the product from Example 39 in 25 ml toluene was added. The reaction was heated at reflux for 3 h, and then cooled to 0° C., and 10 ml H$_2$O was added dropwise. The reaction was then poured into dilute HCl solution and extracted with ethyl acetate. The organic extracts were dried (MgSO$_4$), and evaporated. The resulting product was suspended in 300 ml xylene and 3.14 g pTsOH.H$_2$O. The reaction was stirred at reflux for 18 h, and then evaporated to dryness. The resulting product was purified by chromatography to yield 1.03 g of the trans-isomer, NMR (CDCl$_3$) δ 2.70 (m, 2H), 3.05 (dd, 1H), 3.17 (dd, 1H), 3.37 (dt, 1H), 3.75 (dd, 1H), 3.80 (s, 3H), 4.98 (dd, 2H), 6.72 (d, 1H), 6.91 (d, 1H), 7.20 (t, 1H), 7.22–7.40 (m, 5H). Further elution yielded 2.38 g of the cis-isomer, NMR (CDCl$_3$) δ 2.83 (dd, 1H), 3.03 (dd, 1H), 3.24 (dd, 1H), 3.43 (m, 2H), 3.75 (m, 1H), 3.81 (s, 3H), 4.96 (s, 2H), 6.71 (d, 1H), 6.84 (d, 1H), 7.20 (m, 6H).

EXAMPLE 41

Preparation of cis-2-benzyl-5-methoxy-2,3,4,4a,9,9a-hexahydro-1H-indeno[2,1-c]pyridine hydrochloride The cis-isomer from Example 40 (2.35 g) was dissolved in 100 ml tetrahydrofuran. To the solution was added 2.25 g LiAlH$_4$. The reaction was stirred at 25° C. for 3 h, and then quenched by the addition of 2.35 ml H$_2$O, 2.35 ml 15% NaOH, and 7 0 ml H$_2$O, filtered and the solvent evaporated. The resulting product was treated with ethereal HCl to yield 2.26 g of the desired product as a white solid, mp: 216–8° C. NMR (d$_6$ DMSO) δ 1.70 (m, 1H), 2.00–3.55 (m, 8H), 3.78 (s, 3H), 4.18–4.44 (m, 3H), 6,85 (m,m 2H), 7.16 (m, 1H), 7.40 (m, 3H), 7.58 (m, 1H), 7.70 (m, 1H).

EXAMPLE 42

Preparation of cis-5-methoxy-2,3,4,4a,9,9a-hexahydro-1H-indeno[2,1-c]pyridine hydrochloride The product from Example 41 (1.80 g) was combined with 0.90 g 20% Pd/C. in 100 ml methanol and hydrogenated at 4 atm for 4 h. The reaction was filtered and evaporated to yield 1.08 g of the desired product as a white solid, mp: 140–3° C. NMR (d$_6$ DMSO) δ 1.70 (m, 1H), 2.02 (m, 1H), 2.60 (m, 1H), 2.78–3.30 (m, 7H), 3.77 (s, 3H), 6.80 (d, 1H), 6.84 (d, 1H), 7.15 (t, 1H).

EXAMPLE 43

Preparation of cis-2-(b 3-(3,3-tetramethylene)glutarimidyl)propyl-5-methoxy-2,3,4,4a,9,9a-hexahydro-1H-indeno[2,1-c]pyridine hydrochloride The product from Example 42 (0.479 g) was treated as described in Example 26 to yield the desired product as a white solid, mp: 170–2° C. NMR (d$_6$ DMSO) δ 1.40 (m, 4H), 1.62 (m, 4H), 1.80–3.70 (m, 16H), 2.62 (s, 4H), 3.78 (s, 3H), 6.78 (d, 1H), 6.83 (d, 1H), 7.15 (t, 1H).

Analysis, theoretical (¼.H$_2$O): C, 66.50; H, 7.92; N, 6.20. Found: C, 66.48; H, 7.76; N, 6.12.

EXAMPLE 44

Preparation of cis-2-(4-(3,3-tetramethylene)glutarimidyl)butyl-5-methoxy-2,3,4,4a,9,9a-hexahydro-1H-indeno[2,1-c]pyridine hydrochloride The product from Example 42 (0.479 g) was treated as described in Example 7 to yield, after lyophilization, the desired product as a non-crystalline amorphous powder. NMR (d$_6$ DMSO) δ 1.40 (m, 4H), 1.65 (m, 6H), 1.90–3.70 (m, 16H), 2.62 (s, 4H), 3.78 (s, 3H), 6.78 (d, 1H), 6.87 (d, 1H), 7.17 (t, 1H).

Analysis, theoretical (1.H$_2$O): C, 65.18; H, 8.20; N, 5.85. Found: C, 65.65; H, 7.96; N, 5.83.

EXAMPLE 45

Preparation of cis-5-methoxy-2-propyl-2,3,4,4a,9,9a-hexahydro-1H-indeno[2,1-c]pyridine hydrochloride The product from Example 42 (0.546 g) was treated as described in Example 9 to yield 0.428 g of the desired product as a white solid, mp: 175–7° C. NMR (d$_6$ DMSO) δ 0.90 (t, 3H), 1.20 (m, 4H), 1.95–3.55 (m, 10H), 3.78 (s, 3H), 6.78 (d, 1H), 6.84 (d, 1H), 7.15 (t, 1H).

Analysis, theoretical: C. 68.19; H, 8.58; N, 4.97. Found: C, 68.01; H, 8.55; N, 4.93.

EXAMPLE 46

Preparation of cis-5-hydroxy-2-propyl-2,3,4,4a,9,9a-hexahydro-1H-indeno[2,1-c]pyridine hydrobromide The product from Example 45 (0.563 g) was treated as described in Example 10 to yield 0.247 g of the desired product as a white solid, mp: 204–6° C. NMR (d$_6$ DMSO) δ 0.90 (t, 3H), 1.70 (m, 4H), 2.05–3.55 (m, 10H), 6.60 (d, 1H), 6.70 (d, 1H), 6.95 (t, 1H).

Analysis, theoretical: C, 57.70; H, 7.10; N, 4.49. Found: C, 57.67; H, 7.12; N, 4.43.

EXAMPLE 47

Preparation of trans-2-benzyl-5-methoxy-2,3,4,4a,9,9a-hexahydro-1H-indeno[2,1-c]pyridine hydrochloride The trans-isomer from Example 41 (1.00 g) was treated as described in Example 38 to yield 0.834 g of the desired product as a white solid, mp: >260° C. NMR (d$_6$ DMSO) δ 1.95 (m, 1H), 2.28 (m, 1H), 2.38–3.55 (m, 8H), 3.73 (s, 3H), 4.34 (dd, 2H), 6.80 (d, 1H), 6.84 (d, 1H), 7.13 (t, 1H), 7.48 (m, 3H), 7.62 (m, 2H).Preparation of trans-5-methoxy-2,3,4,4a,9,9a-hexahydro-1H-indeno[2,1-c]pyridine hydrochloride.

EXAMPLE 48

Preparation of trans-5-Methoxy-2,3,4,4a,9,9a-hexahydro-1H-indeno[2,1-c]pyridine hydrochloride The product from Example 47 (0.83 g) was treated as described in Example 42 to yield 0.57 g of the desired product as a white solid, mp: >260° C. NMR (d$_6$ DMSO) δ 1.60–2.10 (m, 4H), 2.55–3.55 (m, 6H), 3.74 (s, 3H), 6.79 (d, 1H), 6.87 (d, 1H), 7.13 (t, 1H).

EXAMPLE 49

Preparation of trans-5-methoxy-2-propyl-2,3,4,4a,9,9a-hexahydro-1H-indeno[2,1-c]pyridine hydrochloride The product from Example 48 (0.118 g) was treated as described in Example 9 to yield 0.075 g of the desired product as a white solid, mp: >260° C. NMR (d$_6$ DMSO) δ 0.92 (t, 3H), 1.73 (m, 2H), 1.85–3.70 (m, 12H), 3.75 (s, 3H), 6.81 (d, 1H), 6.87 (d, 1H), 7.14 (t, 1H).

Analysis, theoretical: C, 68.19; H, 8.54; N, 4.93. Found: C, 68.37; H, 8.54; N, 4.97.

EXAMPLE 50

Preparation of trans-2-(3-(3,3-tetramethylene)glutarimidyl)propyl-5-methoxy-2,3,4,4a,9,9a-hexahydro-1H-indeno[2,1-c]pyridine hydrochloride The product from Example 48 (0.240 g) was treated as described in Example 26 to yield 0.204 g of the desired product as a white solid, mp: 221–5° C. NMR (d$_6$ DMSO) δ 1.43 (m, 4H), 1.55 (m, 4H), 1.90 (m, 4H), 2.20 (m, 2H), 2.62 (s, 4H), 2.30–3.25 (m, 7H), 3.52 (m, 1H), 3.70 (t, 2H), 3.77 (s, 3H), 6.80 (d, 1H), 6.88 (d, 1H), 7.13 (t, 1H).

Analysis, theoretical (¼.H$_2$O): C, 66.50; H, 7.92; N, 6.20. Found: C, 66.39; H, 7.79; N, 6.13.

EXAMPLE 51

Preparation of trans-2-(4-(3,3-tetramethylene)glutarimidyl)butyl-5-methoxy-2,3,4,4a,9,9a-hexahydro-1H-indeno[2,1-c]pyridine hydrochloride The product from Example 48 (0.300 g) was treated as described in Example 7 to yield 0.310 g of the desired product as a white solid, mp: 222–4° C. NMR (d$_6$ DMSO) δ 1.40 (m, 6H), 1.62 (m, 6H), 2.10–3.60 (m, 12H), 2.62 (s, 4H), 3.66 (m, 2H), 3.74 (s, 3H), 6.80 (d, 1H), 6.87 (d, 1H), 7.13 (t, 1H).

Analysis, theoretical: C, 67.73; H, 8.09; N, 6.08. Found: C, 67.43; H, 8.02; N, 5.95.

EXAMPLE 52

Preparation of 5-Bromo-8-methoxy-3,-dihydronaphthalene-1-carbonitrile

5-Bromo-8-methoxy-1,2,3,4-tetrahydronaphthalen-1-one (8.08 g) was dissolved in 80 ml tetrahydrofuran. To the reaction was added 4.9 ml trimethylsilyl cyanide followed by 5 ml 0.5 M LiCN in DMF. After 1.5 h at 25° C., the reaction was quenched in H$_2$O and extracted with ether. The ether extracts were dried (Na$_2$SO$_4$), evaporated, and then added to a refluxing solution of 8.1 g p-toluenesulfonic acid in 135 ml benzene. After 30 min, the reaction was quenched in 5% NaHCO$_3$; the organic extracts were dried (MgSO$_4$) and concentrated to yield, after recrystallization, 6.96 g of the desired product. NMR (CDCl$_3$) δ 2.40 (m, 2H), 2.88 (t, 2H), 3.90 (s, 3H), 6.72 (d, 1H), 6.97 (t, 1H), 7.45 (d, 1H).

EXAMPLE 53

Preparation of 5-Bromo-8-methoxy-1,2,3,4-tetrahydronaphthalene-1,2-dinitrile

Acetic acid (1.60 ml) was added to a solution of 63 ml 0.5 M LiCN in DMF. The solution was cooled to 5° C., and 6.96 g of the product from Example 52 was added. After 15 min at 5° C., the reaction was quenched in H$_2$O, extracted with ether; the extracts were dried (MgSO$_4$), and evaporated to yield 7.1 g of the desired product as a 2:1 mixture of cis/trans-isomers. NMR (CDCl$_3$) δ 2.35 (m, 2H), 2.70 (m, 1H), 3.05 (m, 1H), 3.90 (s, 3H), 4.41 (t, 1/3H), 4.44 (dd, 2/3H), 6.70 (m, 1H), 7.52 (m, 1H).

EXAMPLE 54

Preparation of 8-methoxy-1,2,3,4-tetrahydronaphthalene-1,2-dinitrile

The product from Example 53 (2.90 g) was treated with 3.0 g 10% Pd/BaSO$_4$ and 1.36 g NaOAc in 250 ml methanol and hydrogenated at 4 atm for 4 h. The reaction was filtered and evaporated; and the product was dissolved in ethyl acetate, washed with 5% NaHCO$_3$, dried (MgSO$_4$), and evaporated to yield 1.80 g of the desired product as a colorless oil. NMR (CDCl$_3$) δ 2.30 (m, 2H), 2.80–3.20 (m, 3H), 3.91 (s, 3H), 4.39 (d, ⅓H), 4.46 (d, ⅔H), 6.78 (m, 2H), 7.27 (m, 1H).

EXAMPLE 55

Preparation of cis- and trans-9-methoxy-2,3,3a,4,5,9b-hexahydro-1H-benz[e]isoindole The product from Example 54 (1.00 g) was combined with 4.0 g 20% Pd/C in 250 ml methanol and 8 ml 37% aq. HCl. The reaction was hydrogenated at 4 atm for 72 h at 25° C. After filtration, the solvent was removed and the product was purified by column chromatography (methanol/chloroform/ammonia) to yield 0.51 g of the cis-isomer. NMR (CDCl$_3$) δ 1.70 (m, 2H), 2.39 (m, 1H), 2.54 (dd, 1H), 2.70 (m, 2H), 2.81 (dd, 1H), 3.25 (dd, 1H), 3.30 (t, 1H), 3.60 (dd, 1H), 3.80 (s, 3H), 6.68 (d, 1H), 6.72 (d, 1H), 7.08 (t, 1H). Further elution yield 0.18 g of the trans-isomer. NMR (CDCl$_3$) d 1.60 (m, 1H), 2.04 (m, 2H), 2.78 (m, 2H), 2.97 (m, 2H), 3.36 (dd, 1H), 3.76 (s, 3H), 4.07 (dd, 1H), 6.66 (d, 1H), 6.77 (d, 1H), 7.12 (t, 1H).

EXAMPLE 56

Preparation of cis-9-methoxy-2-propyl-2,3,3a,4,5,9b-hexahydro-1H-benz[e]isoindole The resultant cis-product from Example 55 (0.51 g) was treated with 0.384 g propionic anhydride in 3 ml pyridine for 1 h at 25° C. The reaction was quenched in cold dilute HCl, extracted with ethyl acetate, and the organic extracts were washed with brine, dried (MgSO$_4$), and evaporated. The resultant oil was dissolved in 20 ml tetrahydrofuran and treated with 0.60 g LiAlH$_4$ for 2 h at 25° C. The reaction was quenched with H$_2$O and 15% NaOH, filtered, and evaporated. The product was treated with ethereal HCl to yield 0.520 g of the desired product as a white solid, mp:

164–6° C. NMR (d$_6$ DMSO) δ 0.91 (t, 3H), 1.70 (m, 4H), 2.55–3.75 (m, 9H), 3.78 (s, 3H), 3.95 (m, 1H), 6.77 (d, 1H), 6.83 (d, 1H), 7.17 (t, 1H).

Analysis, theoretical: C, 68.19; H, 8.58; N, 4.97. Found: C, 68.24; H, 8.65; N, 4.96.

EXAMPLE 57

Preparation of trans-9-methoxy-2-propyl-2,3,3a,4,5,9b-hexahydro-1H-benz[e]isoindole The resultant trans-product from Example 55 (0.146 g) was treated as described in Example 56 to yield 0.120 g of the desired product as a white solid, mp: 227–8° C. NMR (d$_6$ DMSO) δ 0.94 (t, 3H), 1.65 (m, 4H), 1.80–3.65 (m, 9H), 3.75 (s, 3H), 4.25 (m, 1H), 6.77 (d, 1H), 6.80 (d, 1H), 7.15 (t, 1H).

Analysis, theoretical (¼.H$_2$O): C, 67.12; H, 8.62; N, 4.89. Found: C, 67.08; H, 8.65; N, 4.79.

EXAMPLE 58

Preparation of cis-9-hydroxy-2-propyl-2,3,3a,4,5,9b-hexahydro-1H-benz[e]isoindole The product from Example 56 (0.618 g) was treated as described in Example 10 to yield 0.425 g of the desired product as a white solid, mp: 180–4° C. NMR (d$_6$ DMSO) δ 0.90 (t, 3H), 1.70 (m, 4H), 2.30–3.65 (m, 8H), 3.80 (m, 1H), 4.05 (m, 1H), 6.60 (d, 1H), 6.67 (d, 1H), 6.95 (t, 1H).

Analysis, theoretical: C, 57.70; H, 7.10; N, 4.49. Found: C, 57.48; H, 7.00. N, 4.42.

EXAMPLE 59

Preparation of cis-2-(4-(3,3-tetramethylene)glutarimidyl)butyl-9-methoxy-2,3,3a,4,5,9b-hexahydro-1H-benz[e]isoindole hydrochloride The resultant cis-product from Example 55 (1.00 g) was treated as described in Example 7 to yield 0.550 g of the desired product as a white solid, mp: 142–4° C. NMR (CDCl$_3$) δ 1.50 (m, 4H), 1.71 (m, 4H), 1.90 (m, 4H), 2.40–3.20 (m, 7H), 2.60 (s, 4H), 3.40–4.03 (m, 6H), 3.80 (s, 3H), 4.40 (m, 1H), 6.69 (d, 1H), 6.73 (d, 1H), 7.16 (t, 1H).

Analysis, theoretical: C, 67.73; H, 8.09; N, 6.08. Found: C, 67.31; H, 7.74; N, 5.81.

EXAMPLE 60

Preparation of 2-(4-(3,3-Tetramethylene)glutarimidyl)butyl-5-chloro-8-hydroxy-1,2,3,3a,8,8,a-hexahydro-indeno-[1,2-c]pyrrole hydrobromide The product from Example 8 (0.400 g) was treated as described in Example 10 to yield 0.407 g of the desired product as a white solid, mp: 171–4° C. NMR (d$_6$ DMSO) δ 1.40 (m, 4H), 1.62 (m, 6H), 2.62 (s, 4H), 2.70 to 4.10 (m, 14H), 6.70 (d, 1H), 7.13 (d, 1H).

Analysis, theoretical (½ H$_2$O): C, 55.34; H, 6.39; N, 5.38. Found: C, 55.52; H, 6.19; N, 5.27.

EXAMPLE 61

Preparation of cis-2-(4-(3,3-tetramethylene)glutarimidyl)butyl-9-hydroxy-2,3,3a,4,5,9b-hexahydro-1H-benz[e]isoindole hydrobromide The product from Example 59 (0.500 g) was treated as described in Example 10 to yield 0.425 g of the desired product as a white solid, mp: 140–5° C. NMR (d$_6$ DMSO) δ 1.50 (m, 4H), 1.55 to 2.00 (m, 10H), 2.60 (s, 4H), 2.65 to 4.50 (m, 12H), 6.60 (d, 1H), 7.02 (m, 2H).

Analysis, theoretical (¾ H$_2$O): C, 59.46; H, 7.29; N, 5.55. Found: C, 59.46; H, 7.03; N, 5.51.

EXAMPLE 62

Preparation of 8-Methoxy-2-(4-(4-morpholin-3,5-dionyl)butyl)-1,2,3,3a,8,8a-hexahydroindeno-[1,2-c]pyrrole hydrochloride The product from Example 6 (0.800 g) was condensed with 1-bromo-4-(4-morpholin-3,5-dionyl)butane (1.05 g) as described in Example 7 to yield 0.725 g of the desired product as a white solid, mp: 160–2° C. NMR (d$_6$ DMSO) δ 1.65 (m, 2H), 1.92 (m, 2H), 2.42 (m, 1H), 2.70 to 3.10 (m, 4H), 3.20 (m, 1H), 3.55 (m, 1H), 3.70 to 4.40 (m, 5H), 3.80 (s, 3H), 4.40 (s, 4H), 6.72 (d, 1H), 6.83 (d, 1H), 7.24 (t, 1H).

Analysis, theoretical (¼ H$_2$O): C, 60.15; H, 6.94; N, 7.01. Found: C, 60.27; H, 6.87; N, 7.02.

EXAMPLE 63

Preparation of trans-2-(4-(3,3-tetramethylene)glutarimidyl)butyl-9-methoxy-2,3,3a,4,5,9b-hexahydro-1H-benz[e]isoindole hydrochloride The trans-product from Example 55 (0.184 g) was treated as described in Example 7 to yield 0.110 g of the desired product as a white solid, mp: 141–3° C. NMR (CDCl$_3$) δ 1.50 (m, 4H), 1.71 (m, 4H), 1.80 to 3.20 (m, 11H), 2.64 (s, 4H), 3.40–4.03 (m, 6H), 3.78 (s, 3H), 4.70 (m, 1H), 6.65 (d, 1H), 6.77 (d, 1H), 7.16 (t, 1H).

Analysis, theoretical (½ H$_2$O): C, 66.44; H, 8.15; N, 5.96. Found: C, 66.27; H, 7.92; N, 5.92.

EXAMPLE 64

Preparation of 8-Methoxy-2-(4-(3a,4,4a,6a,7,7a-hexahydro-4,7-etheno-1H-cyclobut[f]isoindol-1,3-dionyl)-butyl-1,2,3,3a,8,8a-hexahydroindeno-[1,2-c]pyrrole hydrochloride The product from Example 6 (0.451 g) was condensed with 0.81 g 4-bromo-1-(3a,4,4a,6a,7,7a-hexahydro-4,7-etheno-1H-cyclobut[f]isoindol-1,3-dionyl)-butane as described in Example 7 to yield 0.380 g of the desired product as a white solid, mp: 170–2° C. NMR (d$_6$ DMSO) δ 1.48 (m, 4H), 2.40 to 4.10 (m, 21H), 3.79 (s, 3H), 5.82 (m, 2H), 5.90 (s, 2H), 6.83 (m, 2H), 7.22 (t, 1H).

Analysis, theoretical (2 H$_2$O): C, 65.01; H, 7.21; N, 5.42. Found: C, 64.85; H, 6.72; N, 5.35.

EXAMPLE 65

Preparation of
8-Methoxy-2-(4-(3aα,4a,5,6,7a,7aα-hexahydro-4,7-methano-1H-isoindol-1,3(2H)-dionyl)-butyl-1,2,3,3a,8,,8a-hexahydroindeno-[1,2-c]pyrrole hydrochloride The product from Example 6 (0.350 g) was condensed with 0.65 g 1-bromo-4-(3aα,4a,5,6,7a,7aα-hexahydro-4,7-methano-1H-isoindol-1,3(2H)-dionyl)-butane as described in Example 7 to yield 0.410 g of the desired product as a white solid, mp: 164–6° C. NMR (CDCl$_3$) δ 1.18 (m, 2H), 1.60 (m, 6H), 1.92 (m, 2H), 2.42 (q, 1H), 2.70 to 3.95 (m, 13H), 3.82 (s, 3H), 4.20 (m, 2H), 6.72 (d, 1H), 6.85 (d, 1H), 7.23 (t, 1H).

Analysis, theoretical (½ H$_2$O): C, 66.14; H, 7.55; N, 6.17. Found: C, 66.14; H, 7.25; N, 6.10.

EXAMPLE 66

Preparation of
cis-2-(4-(3aα,4a,5,6,7a,7aα-hexahydro-4,7-methano-1H-isoindol-1,3(2H)-dionyl)-butyl-9-methoxy-2,3,3a,4,5,9b-hexahydro-1H-benz[e]isoindole hydrochloride The resultant cis-product from Example 55 (0.700 g) was condensed with 0.92 g 1-bromo-4-(3aα,4a,5,6,7a,7aα-hexahydro-4,7-methano-1H-isoindol-1,3(2H)-dionyl)-butane as described in Example 7 to yield 0.650 g of the desired product as a white solid, mp: 148–50° C. NMR (CDCl$_3$) δ 1.20 (m, 2H), 1.55 (m, 6H), 1.95 (m, 4H), 2.48 to 3.90 (m, 14H), 3.82 (s, 3H), 3.95 (m, 1H), 4.40 (m, 1H), 6.70 (m, 2H), 7.17 (t, 1H).

Analysis theoretical (¼ H$_2$O): C, 67.37; H, 7.72; N, 6.04. Found: C, 67.34; N, 7.61; N, 6.03.

EXAMPLE 67

Preparation of
trans-2-(4-(2-(1,2-benzisothiazolin-3-one-1,1-dioxide))-butyl-9-methoxy-2,3,3a,4,5,9b-hexahydro-1H-benz[e]isoindole hydrochloride The resultant trans-product from Example 55 (0.360 g) was condensed with 0.525 g 4-bromobutyl-2-(1,2-benzisothiazolin-3-one-1,1-dioxide as described in Example 7 to yield 0.319 g of the desired product as a white solid, mp: 258–9 ° C. NMR (d$_6$ DMSO) δ 1.55 (m, 2H), 1.70–2.35 (m, 4H), 2.65–3.50 (m, 8H), 3.72 (s, 3H), 3.60–4.40 (m, 4H), 6.76 (d, 1H), 6.79 (d, 1H), 7.15 (t, 1H), 8.05 (m, 3H), 8.33 (d, 1H).

Analysis theoretical: C, 60.43; H, 6.13; N, 5.87. Found: C, 60.19; H, 6.24; N, 5.75.

EXAMPLE 68

Preparation of
trans-2-(4-(3aα,4a,5,6,7a,7aα-hexahydro-4,7-methano-1H-isoindol-1,3(2H)-dionyl)-butyl-9-methoxy-2,3,3a,4,5,9b-hexahydro-1H-benz[e]-isoindole hydrochloride The resultant trans-product from Example 55 (0.400 g) was condensed with 0.60 g 1-bromo-4-(3aα,4a,5,6,,7a,7aα-hexahydro-4,7-methano-1H-isoindol-1,3(2H)-dionyl)-butane as described in Example 7 to yield 0.349 g of the desired product as a white solid, mp: 180–82 ° C. NMR (d$_6$ DMSO) δ 1.08 (m, 2H), 1.60 (m, 10H), 2.09 (m, 2H), 2.60 (m, 2H), 2.80–3.30 (m, 8H), 3.40 (t, 2H), 3.56 (m, 1H), 3.76 (s, 3H), 4.10 (m, 1H), 6.80 (m, 2H), 7.18 (t, 1H).

Analysis theoretical (½ H$_2$O): C, 66.72; H, 7.75; N, 5.99. Found: C, 66.67; H, 7.59; N, 5.92.

EXAMPLE 69

Preparation of
trans-2-(4-(3,3-tetramethylene)glutarimidyl)propyl-9-methoxy-2,3,3a,4,5,9b-hexahydro-1H-benz[e]isoindole hydrochloride The resultant trans-product from Example 55 (0.719 g) was treated with 0.951 g 1-bromo-3-(3,3-tetramethyleneglutarimidyl)-propane as described in Example 7 to yield 0.492 g of the desired product as a white solid, mp: 212–14 ° C. NMR (d$_6$ DMSO) δ 1.30–2.35 (m, 14H), 2.65 (s, 4H), 2.70–3.50 (m, 6H), 3.55–3.90 (m, 4H), 3.77 (s, 3H), 6.78 (d, 1H), 7.00 (d, 1H), 7.16 (t, 1H).

Analysis theoretical: C, 67.17; H, 7.89; N, 6.23. Found: C, 67.14; H, 7.88; N, 6.23.

EXAMPLE 70

Preparation of
trans-2-(4-(3a,4,4a,6a,7,7a-hexahydro-4,7-etheno-1H-cyclobut[f]isoindol-1,3-dionyl)-butyl)-9-methoxy-2,3,3a,4,5,9b-hexahydro-1H-benz[e]isoindole hydrochloride The resultant trans-product from Example 55 (0.719 g) was treated with 1.11 g 4-bromo-1-(3a,4,4a,6a,7,7a-hexahydro-4,7-etheno-1H-cyclobut[f]isoindol-1,3-dionyl)-butane as described in Example 7 to yield 0.662 g of the desired product as a white solid, mp: 213–14 ° C. NMR (d$_6$ DMSO) δ 1.25–1.70 (m, 8H), 1.85–2.25 (m, 2H), 2.60–3.50 (m, 10H), 3.55–3.90 (m, 4H), 3.75 (s, 3H), 5.88 (m, 4H), 6.78 (d, 1H), 6.80 (d, 1H), 7.17 (t, 1H).

Analysis theoretical: C, 70.36; H, 7.13; N, 5.66. Found: C, 70.24; H, 7.17; N, 5.58.

EXAMPLE 71

Preparation of
2-Oxo-3-carboethoxy-5-(2-bromo-5-methoxyphenyl)-pentanoic acid ethyl ester Potassium t-butoxide (26.94 g) was suspended in 130 ml of anhydrous ether and cooled to 0° C. A solution of 60.24 g ethyl 4-(2-bromo-5-methoxy phenyl)butyrate and 43.84 g diethyl oxalate in 60 ml ether was added dropwise over 20 min. After 2 h at 25° C., the reaction was poured into 400 ml H$_2$O and the aqueous layer was separated, acidified to pH 1 and extracted with ether. The ether layer was dried (MgSO$_4$) and the solvent was evaporated to yield 71.26 g of the desired product as a colorless oil (89%). NMR (CDCl$_3$) δ 1.25 (t, 3H), 1.4 (t, 3H), 2.25 (m, 2H), 2.75 (m, 2H), 3.78 (s, 3H), 4.0–4.5 (m, 5H), 6.64 (dd, 1H), 6.79 (d, 1H), 7.40 (d, 1H).

EXAMPLE 72

Preparation of
5-Bromo-8-methoxy-3,4-dihydronaphthalene-1,2-dicarboxylic acid, ethyl ester The product from Example 71 (70.0 g) was added to 1 kg PPA at 25° C. The reaction was stirred for 40 min, and then quenched in 3 kg ice. The mixture was extracted with ether; and the organic phase was washed with 5% NaHCO$_3$, dried (MgSO$_4$) and evaporated to dryness. The resulting solid was recrystallized from methanol to yield 40.95 g of a light yellow solid. NMR (CDCl$_3$) δ 1.42 (t, 3H), 1.47 (t, 3H), 2.55 (t, 2H) 2.90 (t, 2H), 3.80 (s, 3H), 4.28 (q, 2H), 4.31 (q, 2H), 6.70 (d, 1H), 7.48 (d, 1H).

EXAMPLE 73

Preparation of cis-8-methoxy-1,2,3,4-tetrahydronaphthalene-1,2-dicarboxylic acid, ethyl ester The product from Example 72 (9.08 g) was dissolved in 100 ml Ethanol. To the solution was added 3.55 g NaOAc and 2.27 g 10% Pd/C. The reaction was hydrogenated at 4 atm for 24 h, filtered, evaporated to dryness. The product was dissolved in ether, washed with 5% NaHCO$_3$ solution, dried (MgSO$_4$) and evaporated to dryness to yield 6.89 g of a white solid. NMR (CDCl$_3$) δ 1.20 (t, 3H), 1.32 (t, 3H), 2.08 (m, 2H), 2.80 (m, 2H), 2.94 (m, 1H), 3.80 (s, 3H), 4.12 (m, 4H), 4.47 (d, 1H), 6.68 (d, 1H), 6.76 (d, 1H), 7.15 (t, 1H).

EXAMPLE 74

Preparation of trans-8-methoxy-bis-(1,2-hydroxymethyl)-1,2,3,4-tetrahydronaphthalene A solution of LDA (27 mmol) was prepared in 300 ml THF. To the above solution at 0° C. was added 9.19 g of the product from Example 73. After 30 min, the reaction was quenched in dil HCl, extracted with ether; the organic layer was dried (MgSO$_4$), and evaporated to dryness. The product was dissolved in hexane and cooled to −20° C. for 3 h. The crystalline product was collected (cis-isomer, 2.03 g), and mother liquor was evaporated to dryness (7.03 g). NMR analysis of the mother liquor showed it to be 80% trans-isomer, 20% cis-isomer of the diester. The product from the mother liquor was then added to a suspension of 3.5 g LiAlH$_4$ in 150 ml THF. After 1 h at 25° C., the reaction was quenched (Fieser Workup), and the solvent was evaporated. The product was recrystallized from 3:1 hexane:ethyl acetate to yield 2.95 g of the pure trans-isomer. NMR (CDCl$_3$) δ 1.50 (m, 1H), 1.95–2.30 (m, 4H), 2.70 (t, 2H), 3:22 (m, 1H), 3.53 (m, 2H), 3.64 (m, 1H), 3.81 (s, 3H), 3.82 (m, 1H), 6.70 (d, 1H), 6.72 (d, 1H), 7.10 (t, 1H).

EXAMPLE 75

Preparation of trans-8-methoxy-bis-(1,2-hydroxymethyl)-1,2,3,4-tetrahydronaphthalene-1,2-bis-mesylate The product from Example 74 (2.90 g) was dissolved in 250 ml CH$_2$Cl$_2$ and 9.1 ml triethyl amine. The solution was cooled to 0° C. and 3.12 ml methanesulfonyl chloride was added over 10 min. After 1 h, the reaction was quenched in 5% NaHCO$_3$ solution and extracted with CH$_2$Cl$_2$; the organic extracts were washed with brine, dried (MgSO$_4$) and evaporated to dryness. The product was triturated with hexane and the desired crystalline product (5.00 g) was collected. NMR (CDCl$_3$) δ 1.80 (m, 1H), 2.04 (m, 1H), 2.61 (m, 1H), 2.75 (m, 2H), 2.96 (s, 3H), 3.00 (s, 3H), 3.41 (m, 1H), 3.85 (s, 3H), 4.17 (m, 3H), 4.48 (dd, 1H), 6.71 (d, 1H), 6.73 (d, 1H), 7.17 (t, 1H).

EXAMPLE 76

Preparation of trans-2-((S)-a-methylbenzyl)-9-methoxy-2,3,3a,4,5,9b-hexahydro-1H-benz[e]isoindole hydrochloride The product from Example 75 (1.45 g) was dissolved in 7.5 ml (s)-(−)-a-methylbenzyl amine, and the reaction was heated at 65° C. for 18 h. The reaction was quenched in 5% NaHCO$_3$ solution and extracted with ether; the solvent was dried (K$_2$CO$_3$) and evaporated to dryness. The resulting mixture of two diastereomeric products was purified by silica gel chromatography (65:35 ether:hexane) to yield 0.408 g of a faster moving material. NMR (CDCl$_3$) δ 1.39 (d, 3H), 1.50 (m, 1H), 1.98 (m, 2H), 2.51 (dd, 1H), 2.65 (dd, 1H), 2.75 (m, 1H), 2.88 (dd, 1H), 2.93 (m, 2H), 3.65 (dd, 1H), 3.70 (s, 3H), 3.72 (dd, 1H), 6.62 (d, 1H), 6.74 (d, 1H), 7.07 (t, 1H), 7.30 (m, 5H). The product was converted to its HCl salt, mp: 232–3° C.

Further elution yielded 0.341 g of a slower moving material. NMR (CDCl$_3$) d 1.43 (d, 3H), 1.50 (m, 1H), 1.95 (m, 2H), 2.39 (dd, 1H), 2.80 (m, 5H), 3.58 (dd, 1H), 3.66 (dd, 1H), 3.71 (s, 3H), 6.62 (d, 1H), 6.73 (d, 1H), 7.07 (t, 1H), 7.30 (m, 5H). The product was converted to its HCl salt, mp: 242–4° C.

EXAMPLE 77

Preparation of trans-2-(2)-aminoethyl)-9-methoxy-2,3,3a,4,5,9b-hexahydro-1H-benz[e]isoindole The product from Example 75 (0.918 g) was dissolved in 10 ml ethylenediamine, and the reaction was stirred at 60° C. for 1.5 h. The reaction was quenched in cold dilute NaOH solution and extracted with CH$_2$Cl$_2$; the organic extracts were dried (K$_2$CO$_3$) and evaporated to dryness to yield 0.47 g of the desired product as a colorless oil. NMR (CDCl$_3$) δ 1.55 (m, 4H), 2.03 (m, 2H), 2.52 (dd, 1H), 2.75 (m, 6H), 2.97 (m, 2H), 3.60 (dd, 1H), 3.77 (s, 3H), 6.64 (d, 1H), 6.77 (d, 1H), 7.09 (t, 1H).

EXAMPLE 78

Preparation of trans-2-(3-aminopropyl)-9-methoxy-2,3,3a,4,5,9b-hexahydro-1H-benz[e]isoindole The product from Example 75 (0.946 g) was dissolved in 10 ml 1,3-diaminopropane, and the reaction was stirred at 60° C. for 12 h. The reaction was quenched in cold dilute NaOH solution and extracted with CH$_2$Cl$_2$; the organic extracts were dried (K$_2$CO$_3$) and evaporated to dryness to yield 0.58 g of the desired product as a colorless oil. NMR (CDCl$_3$) δ 1.65 (m, 6H), 2.03 (m, 2H), 2.52 (dd, 1H), 2.75 (m, 6H), 2.97 (m, 2H), 3.60 (dd, 1H), 3.77 (s, 3H), 6.64 (d, 1H), 6.77 (d, 1H), 7.09 (t, 1H).

EXAMPLE 79

Preparation of (−)-trans-9-methoxy-2,3,3a,4,5,9b-hexahydro-1H-benz[e]isoindole hydrochloride The resultant faster moving material (as its HCl salt) from Example 76 (0.550 g) was dissolved in 100 ml methanol, and 0.100 g 10% Pd/C was added. The reaction was hydrogenated at 4 atm H$_2$ pressure for 24 h, filtered and the solvent evaporated to yield 0.253 g of a white solid. [α]$_D^{25°}$ ethanol = −108.8° (c=1.02). NMR (free base) (CDCl$_3$) δ 1.60 (m, 1H), 2.04 (m, 2H), 2.78 (m, 2H), 2.97 (m, 2H), 3.36 (dd, 1H), 3.76 (s, 3H), 4.07 (dd, 1H), 6.66 (d, 1H), 6.77 (d, 1H), 7.12 (t, 1H).

EXAMPLE 80

Preparation of
(+)-trans-9-methoxy-2,3,3a,4,5,9b-hexahydro-1H-benz[e]isoindole hydrochloride The resultant slower moving material (as its HCl salt) from Example 76 (0.470 g) was dissolved in 100 ml methanol, and 0.100 g 10% Pd/C was added. The reaction was hydrogenated at 4 atm $H_2$ pressure for 24 h, filtered and the solvent evaporated to yield 0.281 g of a white solid. $[\alpha]_D^{25°}$ethanol = +104.4° (c=1.08). NMR (free base) (CDCl$_3$) δ 1.60 (m, 1H), 2.04 (m, 2H), 2.78 (m, 2H), 2.97 (m, 2H), 3.36 (dd, 1H), 3.76 (s, 3H), 4.07 (dd, 1H), 6.66 (d, 1H), 6.77 (d, 1H), 7.12 (t, 1H).

EXAMPLE 81

Preparation of trans
9-methoxy-2-(2-(4-fluorobenzamido)ethyl)-2,3,3a,4,5,9b-hexahydro-1H-benz[e]isoindole hydrochloride The product from Example 77 (0.43 g) was treated as described in Example 18 to yield 0.543 g white solid, mp: 222-4° C. NMR (d$_6$ DMSO) δ 1.60 (m, 2H), 2.05 (m, 2H), 2.65-3.50 (m, 6H), 3.55-4.0 (m, 4H), 3.72 (s, 3H), 6.78 (d, 1H), 6.79 (d, 1H), 7.15 (t, 1H), 7.33 (m, 2H), 8.02 (m, 2H), 8.90 (m, 1H).

Analysis theoretical (¼ H$_2$O): C, 64.54; H, 6.50; N, 6.84. Found: C, 64.29; H, 6.42; N, 6.67.

EXAMPLE 82

Preparation of trans
9-methoxy-2-(3-(4-fluorobenzamido)propyl)-2,3,3a,4,5,9b-hexahydro-1H-benz[e]isoindole hydrochloride The product from Example 78 (0.57 g) was treated as described in Example 18 to yield 0.577 g white solid, mp: 199-201° C. NMR (d$_6$ DMSO) δ 1.55 (m, 2H), 2.05 (m, 4H), 2.70-3.50 (m, 6H), 3.60-4.0 (m, 4H), 3.78 (s, 3H), 6.78 (d, 1H), 6.80 (d, 1H), 7.16 (t, 1H), 7.30 (m, 2H), 7.96 (m, 2H), 8.70 (m, 1H).

Analysis theoretical: C, 65.94; H, 6.74; N, 6.69. Found: C, 65.47; H, 6.68; N, 6.63.

EXAMPLE 83

Preparation of
trans-2-(3-(2-(1,2-benzisothiazolin-3-one-1,1-dioxide))-propyl)-9-methoxy-2,3,3a,4,5,9b-hexahydro-1H-benz[e]isoindole hydrochloride The resultant trans-product from Example 55 (0.719 g) was condensed with 1.004 g 3-bromopropyl-2-(1,2-benzisothiazolin-3-one-1,1-dioxide as described in Example 7 to yield 0.119 g of the desired product as a white solid, mp: 224-6° C. NMR (d$_6$ DMSO) δ 1.55 (m, 2H), 1.85-2.30 (m, 4H), 2.70-3.50 (m, 6H), 3.60-4.00 (m, 4H), 3.75 (s, 3H), 6.78 (d, 1H), 6.79 (d, 1H), 7.15 (t, 1H), 8.08 (m, 3H), 8.34 (m, 1H).

Analysis theoretical (¼ H$_2$O): C, 59.09; H, 5.93; N, 5.99. Found: C, 58.88; H, 5.80; N, 5.88.

EXAMPLE 84

Preparation of
cis-2-(4-(2-(1,2-benzisothiazolin-3-one-1,1-dioxide))-butyl)-9-methoxy-2,3,3a,4,5,9b-hexahydro-1H-benz[e]isoindole hydrochloride The resultant cis-product from Example 55 (0.690 g) was condensed with 1.30 g 4-bromobutyl-2-(1,2-benzisothiazolin-3-one-1,1-dioxide as described in Example 7 to yield 0.619 g of the desired product as a white solid, mp: 92-93° C. NMR (CDCl$_3$) δ 1.69 (m, 3H), 2.05 (m, 4H), 2.29 (dd, 1H), 2.55 (m, 5H), 3.08 (dd, 1H), 3.40 (t, 1H), 3.55 (m, 1H), 3.80 (s, 3H), 3.83 (m, 2H), 6.69 (d, 1H), 6.71 (d, 1H), 7.07 (t, 1H), 7.87 (m, 3H), 8.04 (m, 1H).

Analysis theoretical (H$_2$O): C, 58.23; H, 6.31; N, 5.66. Found: C, 58.30; H, 5.86; N, 5.58.

EXAMPLE 85

Preparation of
cis-2-(3-(3,3-tetramethylene)glutarimidyl)propyl-9-methoxy-2,3,3a,4,5,9b-hexahydro-1H-benz[e]isoindole hydrochloride The resultant cis-product from Example 55 (0.60 g) was treated with 1.02 g 3-bromo-(3,3-tetramethylene)-glutarimidylpropane as described in Example 7 to yield 1.06 g of the desired product as a white solid, mp: 163-5° C. NMR (CDCl$_3$) δ 1.48 (m, 4H), 1.69 (m, 8H), 1.97 (t, 1H), 2.20 (dd, 1H), 2.42 (m, 1H), 2.57 (s, 4H), 2.61 (m, 3H), 3.08 (dd, 1H), 3.39 (t, 1H), 3.54 (q, 1H), 3.79 (s, 3H), 3.80 (m, 2H), 6.68 (d, 1H), 6.71 (d, 1H), 7.07 (t, 1H).

Analysis theoretical: C, 67.17; H, 7.89; N, 6.23. Found: C, 67.04; H, 7.89; N, 6.23.

EXAMPLE 86

Preparation of
cis-2-(3-(2-(1,2-benzisothiazolin-3-one-1,1-dioxide))propyl-9-methoxy-2,3,3a,4,5,9b-hexahydro-1H-benz[e]-isoindole hydrochloride The resultant cis-product from Example 55 (0.60 g) was condensed with 1.08 g 3-bromopropyl-2-(1,2-benzisothiazolin-3-one-1,1-dioxide as described in Example 7 to yield 0.509 g of the desired product as a white solid, mp: 132-6° C. NMR (CDCl$_3$) δ 1.69 (m, 3H), 2.05 (m, 2H), 2.29 (dd, 1H), 2.55 (m, 5H), 3.08 (dd, 1H), 3.40 (t, 1H), 3.55 (m, 1H), 3.80 (s, 3H), 3.83 (m, 2H), 6.69 (d, 1H), 6.71 (d, 1H), 7.07 (t, 1H), 7.87 (m, 3H), 8.04 (m, 1H).

Analysis theoretical (½ H$_2$O): C, 58.53; H, 5.98; N, 5.93. Found: C, 58.50; H, 5.99; N, 5.78.

EXAMPLE 87

Preparation of
trans-2-(4-(3a,4,4a,5,6,6a,7,7a-octahydro-4,7-ethano-1H-cyclobut[f]isoindol-1,3-dionyl)-butyl)-9-methoxy-2,3,3a,4,5,9b-hexahydro-1H-benz[e]-isoindole hydrochloride The product from Example 70 (0.880 g) was dissolved in 100 ml ethanol. To the reaction was added 0.16 g 5% Pd/C and the reaction was hydrogenated at 4 atm for 48 h. The reaction was filtered and evaporated, and the product recrystallized from ethanol and ether to yield 0.319 g of the desired product as a white solid, mp: 213-14° C. NMR (CDCl$_3$) δ 1.30 (m, 2H), 1.65 (m, 4H), 1.85-2.45 (m, 10H)l, 2.54 (m, 2H), 2.72 (m, 2H), 3.00 (m, 2H), 3.20 (m, 4H), 3.60 (m, 2H), 3.79 (s, 3H), 3.85 (m, 4H), 6.68 (d, 1H), 6.78 (d, 1H), 7.17 (t, 1H).

Analysis theoretical (½ H$_2$O): C, 68.55; H, 7.93; N, 5.54. Found: C, 68.27; H, 7.79; N, 5.46.

EXAMPLE 88

Preparation of
(−)-trans-2-(4-(3a,4,4a,6a,7,7a-hexahydro-4,7-etheno-1H-cyclobut[f]isoindol-1,3-dionyl)-butyl)-9-methoxy-2,3,3a,4,5,9b-hexahydro-1H-benz[e]-isoindole hydrochloride The product from Example 79 (0.240 g) was treated with 0.353 g 4-bromo-1-(3a,4,4a,6a,7,7a-hexahydro-4,7-etheno-1H-cyclobut[f]isoindol-1,3-dionyl)-butane as described in Example 7 to yield 0.178 g of the desired product as a white solid, mp: 203–4° C. $[\alpha]_D^{25°} = -55.9°$ (Ethanol, c=0.58). NMR (d$_6$ DMSO) δ 1.25–1.70 (m, 8H), 1.85–2.25 (m, 2H), 2.60–3.50 (m, 10H), 3.55–3.90 (m, 4H), 3.75 (s, 3H), 5.88 (m, 4H), 6.78 (d, 1H), 6.80 (d, 1H), 7.17 (t, 1H).

Analysis theoretical: C, 70.36; H, 7.13; N, 5.66. Found: C, 69.82; H, 7.05; N, 5.53.

EXAMPLE 89

Preparation of
(+)-trans-2-(4-(3a,4,4a,6a,7,7a-hexahydro-4,7-etheno-1H-cyclobut[f]isoindol-1,3-dionyl)-butyl)-9-methoxy-2,3,3a,4,5,9b-hexahydro-1H-benz[e]-isoindole hydrochloride The product from Example 80 (0.240 g) was treated with 0.353 g 4-bromo-1-(3a,4,4a,6a,7,7a-hexahydro-4,7-etheno-1H-cyclobut[f]isoindol-1,3-dionyl)-butane as described in Example 7 to yield 0.204 g of the desired product as a white solid, mp: 201–2° C. $[\alpha]_D^{25°} = +52.1°$ (Ethanol, c=0.53). NMR (d$_6$ DMSO) δ 1.25–1.70 (m, 8H), 1.85–2.25 (m, 2H), 2.60–3.50 (m, 10H), 3.55–3.90 (m, 4H), 3.75 (s, 3H), 5.88 (m, 4H), 6.78 (d, 1H), 6.80 (d, 1H), 7.17 (t, 1H).

Analysis theoretical: C, 70.36; H, 7.13; N, 5.66. Found: C, 69.89; H, 7.28; N, 5.59.

EXAMPLE 90

Preparation of
trans-2-(3(2-(1,2-benzisothiazolin-3-one-1,1-dioxide))-propyl)-5-methoxy-2,3,4,4a,9,9a-hexahydro-1H-indeno[2,1-c]-pyridine hydrochloride The product from Example 48 (0.480 g) was treated with 0.730 g 3-bromopropyl-2-(1,2-benzisothiazolin-3-one-1,1-dioxide as described in Example 7 to yield 0.463 g of the desired product as a white solid, mp: 252–3° C. NMR (d$_6$ DMSO) δ 1.90 (m, 2H), 2.22 (m, 4H), 2.58 (m, 2H), 2.80 (m, 2H), 2.95–3.45 (m, 4H), 3.60 (m, 2H), 3.74 (s, 3H), 3.86 (t, 2H), 6.80 (d, 1H), 6.87 (d, 1H), 7.12 (t, 1H), 8.08 (m, 3H), 8.34 (d, 1h).

Analysis theoretical (½ H$_2$O): C, 58.53; H, 5.98; N, 5.94. Found: C, 58.03; H, 5.82; N, 6.11.

EXAMPLE 91

Preparation of
trans-2-(4-(2-(1,2-benzisothiazolin-3-one-1,1-dioxide))-butyl)-5-methoxy-2,3,4,4a,9,9a-hexahydro-1H-indeno[2,1-c]-pyridine hydrochloride The product from Example 48 (0.330 g) was treated with 0.48 g 4-bromobutyl-2-(1,2-benzisothiazolin-3-one-1,1-dioxide as described as described in Example 7 to yield 0.363 g of the desired product as a white solid, mp: 228–30° C. NMR (d$_6$ DMSO) δ 1.90 (m, 4H), 2.22 (m, 4H), 2.58 (m, 2H), 2.80 (m, 2H), 2.95–3.45 (m, 4H), 3.60 (m, 2H), 3.74 (s, 3H), 3.86 (t, 2H), 6.80 (d, 1H), 6.87 (d, 1H), 7.12 (t, 1H), 8.08 (m, 3H), 8.34 (d, 1h).

Analysis theoretical: C, 60.43; H, 6.13; N, 5.78. Found: C, 60.11; H, 6.07; N, 5.78.

EXAMPLE 92

Preparation of
trans-2-(2-(4-fluorobenzamido)ethyl)-5-methoxy-2,3,4,4a,9,9a-hexahydro-1H-indeno[2,1-c]-pyridine hydrochloride The product from Example 48 (0.310 g) was treated with 0.34 g 2-bromo-1-(4-fluorobenzamido)ethane as described as described in Example 7 to yield 0.170 g of the desired product as a white solid, mp: 242–4° C. NMR (d$_6$ DMSO) δ 1.95 (m, 2H), 2.29 (m, 2H), 2.45–2.75 (m, 2H), 2.82 (m, 2H), 3.05–3.45 (m, 4H), 3.60–3.90 (m, 2H), 3.77 (s, 3H), 6.80 (d, 1H), 6.87 (d, 1H), 7.13 (t, 1H), 7.31 (m, 2H), 8.00 (m, 2H), 8.98 (m, 1H).

Analysis theoretical (¼ H$_2$O): C, 64.54; H, 6.52; N, 6.84. Found: C, 64.48; H, 6.52; N, 6.81.

The 5-HT selectivity of the compounds of this invention were demonstrated by testing the compounds in radioligand binding assays. The therapeutic activity of the compounds was demonstrated in vivo by the ability of the compounds to affect arterial blood pressure and/or heart rate in various experimental animals such as the spontaneously hypertensive (SH) rat.

Tissue preparation for the radioligand binding assays was performed as described by Pedigo, Yamamura, and Nelson, *J. Neurochemistry*, 36(1): 220–226 (1980). Male Sprague-Dawley rats (150–200 g) were sacrificed and the brains were rapidly removed and placed on ice. The frontal cortex, including the portion immediately above the striatum and part of the parietal cortex were dissected. Tissues from 6–10 rats were pooled and homogenized in at least 40 volumes of tris-HCl buffer (0.05 M, pH 7.4) using a Brinkman Polytron (setting 5 for 20 seconds). This homogenate was centrifuged (48,000 G for 10 minutes), the pellet resuspended, and the process repeated three more times. Between the second and third washes, the tissue homogenate was incubated for 10 minutes at 37° C. The final pellet was resuspended in 100 volumes of TRIS buffer for use in the binding assay.

Radioligand binding affinity for subtypes of the serotonin receptor was determined by the method of Pedigo, Yamamura, and Nelson, op. cit. Tissue homogenate (0.5 mL) from rat frontal cortex, together with various concentrations of tritiated 5-HT and test compounds were added to glass tubes containing modified tris-HCl buffer to obtain, in each case, a final volume of 2 mL and having the following compositions: 5.7 mM ascorbate, 10 micromolar pargyline, 4 mM CaCl$_2$, 50 mM TRIS buffer; pH 7.4 at 37° C.

Each mixture was incubated for 15 minutes at 37° C. and then vacuum filtered through Whatman GF/B filters followed by three 5 mL washes with cold TRIS buffer. Radioactivity was extracted overnight in 3 mL of scintillation liquid and measured by liquid scintillation spectrometry (50% efficiency). In all experiments, tritiated 5-HT binding was defined as the difference between binding in the absence and in the presence of 10 micromolar unlabeled 5-HT and represented 60–80% of the total radioactivity bound.

Binding parameters for saturation and drug displacement studies were calculated by Scatchard analysis and from Hill plots, respectively. Statistical comparisons of data fitted to a one-site versus a two-site model were made using the method of Hancock, et al., Mol. Pharmacol., 16: 1-9 (1979). The high affinity sites were determined to be identical to the 5-HT$_{1A}$ site by conducting the binding assays in the presence of 1 micromolar siproxatriene, a selective 5-HT$_{1A}$ ligand.

In another study, a group of spontaneously hypertensive male rats were trained to be restrained in a wire mesh cylinder in a warming box, at least two training cycles being conducted before testing. The rats were warmed for about one-hour prior to blood pressure measurement, the warming box being maintained at a constant temperature of 36° C. An occluding cuff attached to a programmed sphygmomanometer was placed near the base of the tail of each rat and the pressure of the cuff was increased automatically from 0 to 250 millimeters of mercury at a rate of 10 mm Hg pressure per second. The total time for each cycle of inflation and deflation of the cuff was 50 seconds and the interval between cycles was one minute. A photocell, placed distally to the cuff, recorded the pulses due to the forward motion of blood flow with each heart beat. As the pressure in the cuff increased, the pulse disappeared completely at the point where the cuff pressure equalled and exceeded the arterial blood pressure. The pulse reappeared during deflation at approximately the same pressure. Five interference free signals were recorded for each rat. Rats with a blood pressure of 180 mm Hg or more during the control period were used in the study.

Blood pressure and heart rate readings were recorded on a Model VII Grass polygraph at various intervals after administration of the test compound. Table 1 shows structure-activity relationships of the compounds of the present invention and their radioligand binding (RLB) ability at the 5-HT1 and 5-HT2 receptors. The "high" and "low" affinity Sites refer to the 5-HT$_{1A}$ and 5-HT$_{1B}$ subtyes of the serotonin receptors. For the in vivo test data, SHR refers to spontaneously hypertensive rats, dosed in milligrams per kilogram (mpk), with the data being expressed in the Table in ±% changes at a particular dosage range. That is to say, "−17.5% at 30" represents a 17.5% decrease in blood pressure at a dose level of 30 mg/kg of body weight.

TABLE 1

| Ex. | 5-HT$_1$ | Hill Slope | High | Low | 5-HT$_2$ | In Vivo Data SHR (mpk, p.o. dose) |
|---|---|---|---|---|---|---|
| 7 | 218 | 0.265 | 1.8 | 8443 | 100 | −28% at 30 mg/kg −14% at 10 mg/kg NA at 3 mg/kg |
| 8 | 714 | 0.41 | 19 | 15000 | 64 | −37% at 30 mg/kg |
| 9 | 902 | 0.43 | 154 | 13500 | 2661 | Not tested |
| 10 | 488 | 0.40 | 115 | 9990 | 10000 | Not tested |
| 19 | 262 | 0.33 | 1.13 | 2031 | 96 | −9% at 30 mg/kg |
| 20 | 1841 | 0.448 | — | — | 511 | NA at 30 mg/kg |
| 21 | 438 | 0.546 | — | — | 345 | −28% at 30 mg/kg −16% at 10 mg/kg |
| 22 | 1090 | 0.463 | — | — | 338 | −16 at 30 mg/kg |
| 23 | 1730 | 0.455 | — | — | 659 | −12% at 30 mg/kg |
| 24 | 404 | 0.563 | — | — | 471 | NA at 30 mg/kg |
| 26 | 3300 | 0.56 | — | — | 479 | −23% at 30 mg/kg |
| 27 | 3315 | 0.38 | — | — | 3467 | NA at 30 mg/kg |
| 28 | 722 | 0.62 | — | — | 1279 | Not tested |
| 29 | 3634 | 0.62 | — | — | 1754 | −19% at 30 mg/kg |
| 30 | 533 | 0.37 | 14 | 7240 | 32 | −11% at 30 mg/kg |
| 31 | 457 | 0.445 | 31 | 3720 | 204 | Not tested |
| 32 | 992 | 0.539 | 63 | 5140 | 224 | Not tested |
| 33 | 1748 | 0.490 | — | — | 651 | Not tested |
| 43 | 3125 | 0.39 | — | — | 19.8 | −17.5% at 30 mg/kg |
| 44 | 505 | 0.46 | 54 | 18700 | 40 | NA at 30 mg/kg |
| 50 | 279 | 0.45 | 31 | 6045 | 13.7 | Not tested |
| 51 | 60 | 0.26 | 1.4 | 724 | 27 | −36% at 30 mg/kg |
| 59 | 73 | 0.372 | 0.34 | 330 | 91 | −24% at 30 mg/kg |
| 60 | 1843 | 0.34 | — | — | 91 | −23% at 30 mg/kg |
| 61 | 36 | 0.46 | 1.1 | 480 | 221 | −19% at 30 mg/kg |
| 64 | 283 | 0.33 | 2.9 | 7119 | 74 | Not tested |
| 65 | 647 | 0.35 | 7.21 | 5490 | 96 | NA at 30 mg/kg |
| 67 | 19 | 0.328 | 3.3 | 146 | 189 | −22% at 10 mg/kg |
| 68 | 28 | 0.434 | 5.8 | 691 | 42 | −33% at 30 mg/kg |
| 69 | 163 | 0.625 | — | — | 187 | −8% at 10 mg/kg |
| 70 | 13.5 | 0.42 | 0.77 | 250 | 9 | −32% at 10 mg/kg |
| 81 | 79 | 0.634 | — | — | 101 | −22% at 10 mg/kg |
| 82 | 79 | 0.599 | 3.0 | 389 | 1314 | −7% at 10 mg/kg |
| 83 | 23 | 0.664 | — | — | 26 | NA at 10 mg/kg |
| 84 | 21.8 | 0.634 | 2.4 | 146 | 303 | −20% at 30 mg/kg |
| 85 | 31 | 0.303 | 6.5 | 401 | 60 | −27% at 30 mg/kg |
| 86 | 22.6 | 0.677 | — | — | 8.9 | NA at 10 mg/kg |
| 87 | 45 | 0.772 | — | — | 35 | Not tested |
| 88 | 278 | 0.594 | 0.55 | 167 | 54 | −22% at 3 mg/kg |
| 89 | 53 | 0.675 | 3.50 | 840 | 11 | −12% at 10 mg/kg |
| 90 | 22 | 0.369 | 0.8 | 602 | 3.9 | −18% at 10 mg/kg |
| 91 | 26 | 0.618 | 8.4 | 266 | 31 | −17% at 30 mg/kg |
| 92 | 43 | 0.394 | 4.4 | 982 | 30 | −18% at 10 mg/kg |

Although the present invention has been described in connection with the presently preferred embodiments, those skilled in the art will recognize that changes and modifications can be used in the practice of this invention without departing from the scope of the invention as it is defined in the appended claims. It is intended that such changes and modifications be covered by the following claims.

We claim:
1. A compound of the formula

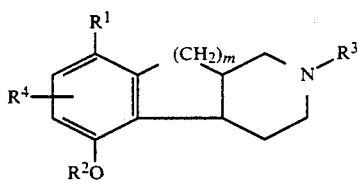

wherein
R¹ is hydrogen or an electron withdrawing group selected from the group consisting of
halogen,
mercapto,
acylmercapto,
alkylsulfido,
nitro,
cyano,
acetyl,
halomethyl, and
alkoxyalkylene;
R² is hydrogen, lower alkyl, or aralkyl;
m is an integer having a value of from 1 to 3;
R⁴ is a member selected from the group consisting of
hydrogen,
halogen,
lower alkyl,
lower alkoxy, and
aryl(lower alkyl);
R³ is a member selected from the group consisting of
hydrogen,
lower alkyl,
lower alkoxy,
arylamidoalkylene,
arylalkylene,
aryl(lower alkyl)amidoalkylidene,
aryl(lower alkyl)amidoalkylene, and
benzoalkylenedioxyalkylene,
a) a group of the formula:

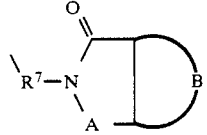

wherein
B is benzo, cyclohexyl, or a bicyclo ring of the structure

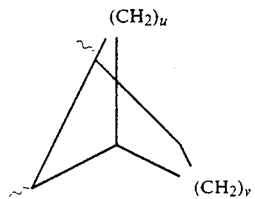

wherein u and v are independent integers of from 1 to 3;
A is CO, SO, or SO₂, and
R⁷ is a bivalent aliphatic hydrocarbon;
b) a group of the formula

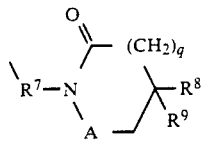

wherein
q is 0 or 1,
R⁸ and R⁹ are independently hydrogen or lower alkyl, or
R⁸ and R⁹ taken together form a ring of from 5 to 7 members, and
A and R⁷ are as defined above;
c) a group of the formula

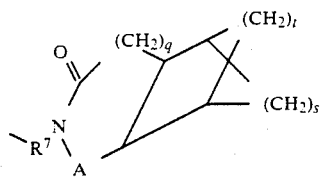

wherein
s and t are independent integers of from 1 to 3,
q, A, and R⁷ are as defined above;
(d) a group of the formula

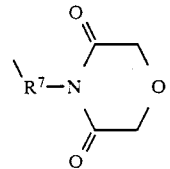

wherein R⁷ is as defined above; and
(e) a group of the formula

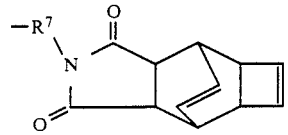

wherein R⁷ is as defined above;
with the proviso that when q is 1, A is only C=O; or a pharmaceutically acceptable salt thereof.

2. A compound as defined by claim 1 represented by the formula

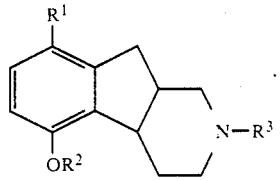

wherein R¹, R², and R³ are as defined therein.

3. A compound as defined by claim 1 wherein R³ is selected from the group consisting of

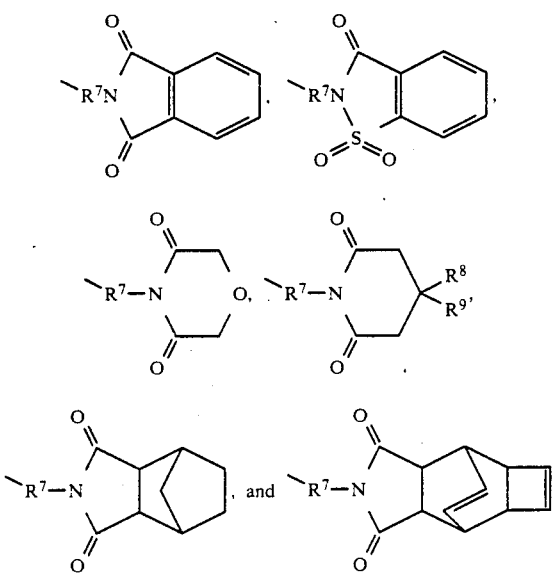

where $R^7$, $R^8$, and $R^9$ are as defined therein.

4. A compound as defined by claim 2 selected from the group consisting of
cis-2-benzyl-5-methoxy-2,3,4,4a,9,9a-hexahydro-1H-indeno[2,1-c]pyridine;
trans-2-benzyl-5-methoxy-2,3,4,4a,9,9a-hexahydro-1H-indeno[2,1-c]pyridine;
cis-5-methoxy-2,3,4,4a,9,9a-hexahydro-1H-indeno[2,1-c]pyridine;
trans-5-methoxy-2,3,4,4a,9,9a-hexahydro-1H-indeno[2,1-c]pyridine;
cis-5-methoxy-2-propyl-2,3,4,4a,9,9a-hexahydro-1H-indeno[2,1-c]pyridine;
cis-5-hydroxy-2-propyl-2,3,4,4a,9,9a-hexahydro-1H-indeno[2,1-c]pyridine;
trans-5-methoxy-2-propyl-2,3,4,4a,9,9a-hexahydro-1H-indeno[2,1-c]pyridine;
cis-2-(3-(3,3-tetramethylene)glutarimidyl)propyl-5-methoxy-2,3,4,4a,9,9a-hexahydro-1H-indeno[2,1-c]pyridine;
trans-2-(3-(3,3-tetramethylene)glutarimidyl)propyl-5-methoxy-2,3,4,4a,9,9a-hexahydro-1H-indeno[2,1-c]pyridine;
cis-2-(4-(3,3-tetramethylene)glutarimidyl)butyl-5-methoxy-2,3,4,4a,9,9a-hexahydro-1H-indeno[2,1-c]pyridine;
trans-2-(4-(3,3-tetramethylene)glutarimidyl)butyl-5-methoxy-2,3,4,4a,9,9a-hexahydro-1H-indeno[2,1-c]pyridine;
trans 2-(3-(2-(1,2-benzoisothiazolin-3-one-1,1dioxide))-propyl)-5-methoxy-2,3,4,4a,9,9a-hexahydro-1H-indeno[2,1-c]pyridine;
trans 2-(4-(2-(1,2-benzoisothiazolin-3-one-1,1dioxide))-butyl)-5-methoxy-2,3,4,4a,9,9a-hexahydro-1H-indeno[2,1-c]pyridine; and
trans 2-(2-(4-fluorobenzamido)ethyl)-5-methoxy-2,3,4,4a,9,9a-hexahydro-1H-indeno[2,1-c]pyridine; or a pharmaceutically acceptable salt thereof.

5. A method of treating hypertension in a mammal in need of such treatment comprising administering to such a mammal a therapeutically effective amount of a compound as defined by claim 1.

6. A pharmaceutical composition comprising an antihypertensive effective amount of a compound as defined by claim 1 in combination with a pharmaceutically acceptable carrier.

7. A method of treating anxiety in a mammal in need of such treatment comprising administering to a mammal in need of such treatment a therapeutically effective amount of a compound as defined by claim 1.

* * * * *